US011965154B2

(12) United States Patent
Spindler et al.

(10) Patent No.: US 11,965,154 B2
(45) Date of Patent: Apr. 23, 2024

(54) DETECTION OF NUCLEASE EDITED SEQUENCES IN AUTOMATED MODULES AND INSTRUMENTS

(71) Applicant: Inscripta, Inc., Boulder, CO (US)

(72) Inventors: Eileen Spindler, Boulder, CO (US); Isaac Wagner, Boulder, CO (US); Clint Davis, Boulder, CO (US); Julia Swavola, Boulder, CO (US); Phillip Belgrader, Pleasanton, CA (US)

(73) Assignee: Inscripta, Inc., Pleasanton, CA (US)

( * ) Notice: Subject to any disclaimer, the term of this patent is extended or adjusted under 35 U.S.C. 154(b) by 1049 days.

(21) Appl. No.: 16/545,097

(22) Filed: Aug. 20, 2019

(65) Prior Publication Data

US 2020/0071660 A1    Mar. 5, 2020

Related U.S. Application Data

(60) Provisional application No. 62/795,739, filed on Jan. 23, 2019, provisional application No. 62/724,851, filed on Aug. 30, 2018.

(51) Int. Cl.
| | | |
|---|---|---|
| *C12N 1/20* | (2006.01) |
| *B01L 3/00* | (2006.01) |
| *C12M 1/00* | (2006.01) |
| *C12M 1/42* | (2006.01) |
| *C12M 3/00* | (2006.01) |
| *C12M 3/04* | (2006.01) |
| *C12N 9/22* | (2006.01) |
| *C12N 13/00* | (2006.01) |
| *G01N 35/00* | (2006.01) |
| *G01N 35/10* | (2006.01) |

(52) U.S. Cl.
CPC ............. *C12N 1/20* (2013.01); *B01L 3/502* (2013.01); *C12M 27/10* (2013.01); *C12M 29/04* (2013.01); *C12M 35/00* (2013.01); *C12M 35/02* (2013.01); *C12M 45/00* (2013.01); *C12N 9/22* (2013.01); *C12N 13/00* (2013.01); *G01N 35/00722* (2013.01); *G01N 35/10* (2013.01); *B01L 2200/16* (2013.01); *B01L 2300/087* (2013.01); *C12M 23/44* (2013.01); *G01N 2035/009* (2013.01)

(58) Field of Classification Search
CPC ...... C12N 1/20; C12N 13/00; C12N 2310/20; C12N 9/22; B01L 3/502; B01L 2200/16; B01L 2300/087; C12M 23/44; C12M 27/10; C12M 29/04; C12M 35/00; C12M 35/02; C12M 45/00; C12M 47/10; C12M 41/08; G01N 35/00722; G01N 35/10; G01N 2035/009
See application file for complete search history.

(56) References Cited

U.S. PATENT DOCUMENTS

| | | |
|---|---|---|
| 4,833,080 A | 5/1989 | Brent et al. |
| 4,959,317 A | 9/1990 | Sauer et al. |
| 5,464,764 A | 11/1995 | Capecchi et al. |
| 5,487,992 A | 1/1996 | Capecchi et al. |
| 5,627,059 A | 5/1997 | Capecchi et al. |
| 5,631,153 A | 5/1997 | Capecchi et al. |
| 5,654,182 A | 8/1997 | Wahl et al. |
| 5,677,177 A | 10/1997 | Wahl et al. |
| 5,710,381 A | 1/1998 | Atwood et al. |
| 5,885,836 A | 3/1999 | Wahl et al. |
| 5,888,732 A | 3/1999 | Hartley et al. |
| 6,074,605 A | 6/2000 | Meserol et al. |
| 6,143,527 A | 11/2000 | Pachuk et al. |
| 6,150,148 A | 11/2000 | Nanda et al. |
| 6,204,061 B1 | 3/2001 | Capecchi et al. |
| 6,277,608 B1 | 8/2001 | Hartley et al. |
| 6,365,373 B2 | 4/2002 | Presta et al. |
| 6,482,619 B1 | 11/2002 | Rubinsky et al. |
| 6,509,156 B1 | 1/2003 | Stewart et al. |
| 6,654,636 B1 | 11/2003 | Dev et al. |
| 6,689,610 B1 | 2/2004 | Capecchi et al. |
| 6,746,441 B1 | 6/2004 | Hofmann et al. |
| 6,774,279 B2 | 8/2004 | Dymecki |
| 6,916,632 B2 | 7/2005 | Chesnut et al. |
| 6,956,146 B2 | 10/2005 | Wahl et al. |
| 7,029,916 B2 | 4/2006 | Dzekunov et al. |
| 7,112,715 B2 | 9/2006 | Chambon et al. |
| 7,141,425 B2 | 11/2006 | Dzekunov et al. |
| 7,422,889 B2 | 9/2008 | Sauer et al. |
| 8,110,122 B2 | 2/2012 | Alburty et al. |
| 8,110,360 B2 | 2/2012 | Serber et al. |
| 8,153,432 B2 | 4/2012 | Church et al. |

(Continued)

FOREIGN PATENT DOCUMENTS

| | | |
|---|---|---|
| CN | 2397122 Y | 9/2000 |
| EP | 2135626 A1 | 12/2009 |

(Continued)

OTHER PUBLICATIONS

Valdez-Cruz et al. Production of recombinant proteins in *E. coli* by the heat inducible expression system based on the phage lambda pL and/or pR promoters. Microbial Cell Factories 2010, 9:18, 16 pages (Year: 2010).*
Apel et al. Nucleic Acids Research (2017; online pub. Nov. 2016), 45(1), 496-508. (Year: 2016).*
Bao, et al., "Genome-scale engineering of *Saccharomyces cerevisiae* with single-nucleotide precision", Nature Biotechnology, doi:10. 1038/nbt.4132, pp. 1-6 (May 7, 2018).
Dicarlo, et al., "Genome engineering in *Saccharomyces cervisiae* using CRISPR-Case systems", Nucleic Acids Research, 41(7):4336-43 (2013).

(Continued)

*Primary Examiner* — Sean C. Barron
(74) *Attorney, Agent, or Firm* — Arnold & Porter Kaye Scholer LLP

(57) ABSTRACT

The present disclosure provides modules, instruments and methods to enrich for cells edited via nucleic acid-guided nuclease editing of live cells.

17 Claims, 18 Drawing Sheets

(56) References Cited

U.S. PATENT DOCUMENTS

| | | |
|---|---|---|
| 8,332,160 B1 | 12/2012 | Platt et al. |
| 8,569,041 B2 | 10/2013 | Church et al. |
| 8,584,535 B2 | 11/2013 | Page et al. |
| 8,584,536 B2 | 11/2013 | Page et al. |
| 8,667,839 B2 | 3/2014 | Kimura |
| 8,667,840 B2 | 3/2014 | Lee et al. |
| 8,677,839 B2 | 3/2014 | Page et al. |
| 8,677,840 B2 | 3/2014 | Page et al. |
| 8,697,359 B1 | 4/2014 | Zhang et al. |
| 8,726,744 B2 | 5/2014 | Alburty et al. |
| 8,758,623 B1 | 6/2014 | Alburty et al. |
| 8,921,332 B2 | 12/2014 | Choulika et al. |
| 8,926,977 B2 | 1/2015 | Miller et al. |
| 8,932,850 B2 | 1/2015 | Chang et al. |
| 9,029,109 B2 | 5/2015 | Hur et al. |
| D731,634 S | 6/2015 | Page et al. |
| 9,063,136 B2 | 6/2015 | Talebpour et al. |
| 9,260,505 B2 | 2/2016 | Weir et al. |
| 9,361,427 B2 | 6/2016 | Hillson |
| 9,499,855 B2 | 11/2016 | Hyde et al. |
| 9,534,989 B2 | 1/2017 | Page et al. |
| 9,546,350 B2 | 1/2017 | Dzekunov et al. |
| 9,593,359 B2 | 3/2017 | Page et al. |
| 9,738,918 B2 | 8/2017 | Alburty et al. |
| 9,790,490 B2 | 10/2017 | Zhang et al. |
| 9,896,696 B2 | 2/2018 | Begemann et al. |
| 9,982,278 B2 | 5/2018 | Gill et al. |
| 9,982,279 B1 | 5/2018 | Gill et al. |
| 9,988,624 B2 | 6/2018 | Serber et al. |
| 10,017,760 B2 | 7/2018 | Gill et al. |
| 10,240,167 B2 | 3/2019 | Gill et al. |
| 10,253,316 B2 | 4/2019 | Masquelier et al. |
| 10,266,849 B2 | 4/2019 | Gill et al. |
| 10,266,851 B2 | 4/2019 | Chen |
| 10,323,242 B1 | 6/2019 | Masquelier et al. |
| 10,323,258 B2 | 6/2019 | Bernate et al. |
| 10,329,559 B1 | 6/2019 | Masquelier et al. |
| 10,351,877 B2 | 7/2019 | Gill et al. |
| 10,362,442 B2 | 7/2019 | Eldic |
| 10,415,058 B2 | 9/2019 | Bernate et al. |
| 10,421,959 B1 | 9/2019 | Masquelier et al. |
| 10,435,662 B1 | 10/2019 | Masquelier et al. |
| 10,435,713 B2 | 10/2019 | Bernate et al. |
| 10,435,715 B2 | 10/2019 | Gill et al. |
| 10,443,031 B1 | 10/2019 | Masquelier et al. |
| 10,443,074 B2 | 10/2019 | Bernate et al. |
| 10,465,185 B1 | 11/2019 | Masquelier et al. |
| 10,465,207 B2 | 11/2019 | Garst et al. |
| 10,550,363 B1 | 2/2020 | Garst et al. |
| 10,738,327 B2 | 8/2020 | Bernate et al. |
| 10,907,178 B2 | 2/2021 | Bernate et al. |
| 10,947,532 B2 | 2/2021 | Masquelier et al. |
| 11,053,507 B2 | 3/2021 | Tian et al. |
| 2003/0059945 A1 | 3/2003 | Dzekunov et al. |
| 2003/0073238 A1 | 4/2003 | Dzekunov et al. |
| 2003/0104588 A1 | 6/2003 | Orwar et al. |
| 2004/0110253 A1 | 6/2004 | Kappler et al. |
| 2004/0115784 A1 | 6/2004 | Dzekunov et al. |
| 2004/0171156 A1 | 9/2004 | Hartley et al. |
| 2005/0064584 A1 | 3/2005 | Bargh |
| 2005/0118705 A1 | 6/2005 | Rabbitt et al. |
| 2006/0001865 A1 | 1/2006 | Bellalou et al. |
| 2006/0224192 A1 | 10/2006 | Dimmer et al. |
| 2007/0105206 A1 | 5/2007 | Lu et al. |
| 2007/0231873 A1 | 10/2007 | Ragsdale |
| 2007/0249036 A1 | 10/2007 | Ragsdale et al. |
| 2008/0138877 A1 | 6/2008 | Dzekunov et al. |
| 2010/0055790 A1 | 3/2010 | Simon |
| 2010/0076057 A1 | 3/2010 | Sontheimer et al. |
| 2011/0009807 A1 | 1/2011 | Kjeken et al. |
| 2011/0065171 A1 | 3/2011 | Dzekunov et al. |
| 2011/0213288 A1 | 9/2011 | Choi et al. |
| 2011/0236962 A1 | 9/2011 | Loebbert et al. |
| 2012/0156786 A1 | 6/2012 | Bebee |
| 2013/0005025 A1 | 1/2013 | Church et al. |
| 2013/0196441 A1 | 8/2013 | Rubinsky et al. |
| 2014/0068797 A1 | 3/2014 | Doudna et al. |
| 2014/0121728 A1 | 5/2014 | Dhillon et al. |
| 2014/0199767 A1 | 7/2014 | Barrangou et al. |
| 2014/0273226 A1 | 9/2014 | Wu et al. |
| 2014/0350456 A1 | 11/2014 | Caccia |
| 2015/0098954 A1 | 4/2015 | Hyde et al. |
| 2015/0159174 A1 | 6/2015 | Frendewey et al. |
| 2015/0176013 A1 | 6/2015 | Musunuru et al. |
| 2015/0191719 A1 | 7/2015 | Hudson et al. |
| 2015/0225732 A1 | 8/2015 | Williams et al. |
| 2015/0297887 A1 | 10/2015 | Dhillon et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0168592 A1 | 6/2016 | Church et al. |
| 2016/0272961 A1 | 9/2016 | Lee |
| 2016/0281047 A1 | 9/2016 | Chen et al. |
| 2016/0289673 A1 | 10/2016 | Huang et al. |
| 2016/0298074 A1 | 10/2016 | Dai |
| 2016/0298134 A1 | 10/2016 | Chen et al. |
| 2016/0310943 A1 | 10/2016 | Woizenko et al. |
| 2016/0354487 A1 | 12/2016 | Zhang et al. |
| 2016/0367991 A1 | 12/2016 | Cepheid |
| 2017/0002339 A1 | 1/2017 | Barrngou et al. |
| 2017/0029805 A1 | 2/2017 | Li et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0218355 A1 | 8/2017 | Buie et al. |
| 2017/0240922 A1 | 8/2017 | Gill et al. |
| 2017/0283761 A1 | 10/2017 | Corso |
| 2017/0307606 A1 | 10/2017 | Hallock |
| 2017/0349874 A1 | 12/2017 | Jaques et al. |
| 2018/0023045 A1 | 1/2018 | Hallock et al. |
| 2018/0028567 A1 | 2/2018 | Li et al. |
| 2018/0051327 A1 | 2/2018 | Blainey et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0169148 A1 | 6/2018 | Adair et al. |
| 2018/0179485 A1 | 6/2018 | Borenstein et al. |
| 2019/0017072 A1 | 1/2019 | Ditommaso et al. |
| 2019/0169605 A1 | 6/2019 | Masquelier et al. |
| 2020/0080045 A1 | 3/2020 | Bernate et al. |
| 2020/0190461 A1 | 6/2020 | Bernate et al. |

FOREIGN PATENT DOCUMENTS

| | | |
|---|---|---|
| EP | 2240238 | 10/2010 |
| EP | 2395087 | 12/2011 |
| EP | 3030652 | 6/2016 |
| EP | 1766004 | 8/2016 |
| EP | 3199632 A1 | 8/2017 |
| EP | 2459696 | 11/2017 |
| WO | WO 2003/057819 | 7/2001 |
| WO | WO 2003/087341 | 10/2003 |
| WO | WO 2009/091578 | 7/2009 |
| WO | WO 2010079430 | 7/2010 |
| WO | WO 2011/072246 | 6/2011 |
| WO | WO 2011/143124 | 11/2011 |
| WO | WO2012012779 A3 | 1/2012 |
| WO | WO 2013/142578 | 9/2013 |
| WO | WO 2013/176772 | 11/2013 |
| WO | WO 2014/018423 | 1/2014 |
| WO | WO2014/144495 A1 | 9/2014 |
| WO | WO 2015/021270 | 2/2015 |
| WO | WO 2016/003485 | 1/2016 |
| WO | WO 2016/054939 | 4/2016 |
| WO | WO 2016/145290 | 9/2016 |
| WO | WO2017/053902 A1 | 3/2017 |
| WO | WO 2017/078631 | 5/2017 |
| WO | WO2017/174329 A1 | 10/2017 |
| WO | WO 2018/015544 | 1/2018 |
| WO | WO2018/031950 A1 | 2/2018 |

(56) References Cited

FOREIGN PATENT DOCUMENTS

WO     WO2018/083339 A1     5/2018
WO     WO 2018/191715     10/2018

OTHER PUBLICATIONS

Eklund, et al., "Altered target site specificity variants of the I-Ppol His-Cys bis homing endonuclease" Nucleic Acids Research, 35(17):5839-50 (2007).
Garst, et al., "Genome-wide mapping of mutations at single-nucleotide resolution for protein, metabolic and genome engineering", Nature Biotechnology, 35(1):48-59 (2017).
Boles, et al., "Digital-to-biological converter for on-demand production of biologics", Nature Biotechnology, doi:10.1038/nbt.3859 (May 29, 2017).
Hsu, et al., "DNA targeting specificity of RNA-guided Cas9 nucleases", Nature Biotechnology, 31(9):827-32 (2013).
Jiang, et al., "RNA-guided editing of bacterial genomes using CRISPR-Cas systems", Nature Biotechnology, 31(3):233-41 (2013).
Jinek, et al., "A Programmable Dual-RNA-Guided DNA Endonuclease in Adaptive Bacterial Immunity", Science, 337:816-20 (2012).
Pines, et al., "Codon Compression Algorithms for Saturation Mutagenesis", ACS Synthetic Biology, 4:604-14 (2015).
Verwaal, et al., "CRISPR/Cpfl enables fast and simple genome editing of *Saccaramyces cerevisiae*", Yeast, 35:201-11 (2018).
Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).
Roy, et cl., "Multiplexed precision genome editing with trackable genomic barcodes in yeast", Nature Biotechnolgy, doi:10.1038/nbt.4137, pp. 1-16 (2018).
Bessa et al., "Improved gap repair cloning in yeast: treatment of the gapped vector with Taq DNA polymerase avoids vector self-ligation," Yeast, 29(10):419-23 (2012).
Boch, "TALEs of genome targeting," Nature Biotechnology vol. 29, pp. 135-136 (2011).
Campbell et al., "Targeting protein function: the expanding toolkit for conditional disruption," Biochem J., 473(17):2573-2589 (2016).
Casini et al., "Bricks and blueprints: methods and standards for DNA assembly," Nat Rev Mol Cell Biol., (9):568-76 (2015).
Chica et al., "Semi-rational approaches to engineering enzyme activity: combining the benefits of directed evolution and rational design," Current Opinion in Biotechnology, 16(4): 378-384 (2005).
Cramer et al., "Functional association between promoter structure and transcript alternative splicing," PNAS USA, 94(21):11456-60 (1997).
Dalphin et al., "Transterm: A Database of Translational Signals," Nucl. Acids Res., 24(1): 216-218 (1996).
Datsenko and Wanner, "One-step inactivation of chromosomal genes in *Escherichia coli* K-12 using PCR products", PNAS USA, 97(12):6640-5 (2000).
De Kok et al., "Rapid and reliable DNA assembly via ligase cycling reaction," ACS Synth Biol., 3(2):97-106 (2014).
Desmet et al., "Human Splicing Finder: an online bioinformatics tool to predict splicing signals," Nucleic Acids Res., 37(9):e67 (2009).
Divina et al., "Ab Initio prediction of mutation-induced cryptic splice-site activation and exon skipping," European Journal of Human Genetics, 17:759-765 (2009).
Dong, "Establishment of a highly efficient virus-inducible CRISPR/Cas9 system in insect cells," Antiviral Res., 130:50-7(2016).
Durai et al., "Zinc finger nucleases: custom-designed molecular scissors for genome engineering of plant and mammalian cells", Nucleic Acids Res., 33(18):5978-90 (2005).
Engler et al., "PLOS One, A One Pot, One Step, Precision Cloning Method with High Throughput Capability," 3(11):e3647 (2008).

Epinat et al., "A novel engineered meganuclease induces homologous recombination in eukaryotic cells, e.g., yeast and mammalian cells", Nucleic Acids Research, 31(11): 2952-2962.
Faber et al., "Genome-wide prediction of splice-modifying SNPs in human genes using a new analysis pipeline called AASsites," BMC Bioinformatics, 12(suppl 4):S2 (2011).
Farasat et al., "A Biophysical Model of CRISPR/Cas9 Activity for Rational Design of Genome Editing and Gene Regulation," PLOS Comput Biol., 29:12(1):e1004724 (2016).
Adamo, et al., "Flow-through comb electroporation device for delivery of macromolecules", Analytical Chemistry, 85(3):1637-41 (2015).
Greger et al., "Balancing transcriptional interference and initiation on the GAL7 promoter of *Saccharomyces cerevisiae*," PNAS, 97(15):8415-20 (2000).
Juan et al., "Histone deacetylases specifically down-regulate p53-dependent gene activation," Journal of Biological Chemistry 275.27 (2000): 20436-20443.
Kadonaga et al., "Regulation of RNA polymerase II transcription by sequence-specific DNA binding factors", Cell, 116(2):247-57 (2004).
Lee et al., "Targeted chromosomal deletions in human cells using zinc finger nucleases", Genome Res., 20 (1):81-9 (2009).
Lefevre et al., "Alanine-stretch scanning mutagenesis: a simple and efficient method to probe protein structure and function, "Nucleic Acids Research, vol. 25(2):447-448 (1997).
Liu et al., "A chemical-inducible CRISPR-Cas9 system for rapid control of genome editing", Nature Chemical Biology, 12:980-987(2016).
Miller et al., "A Tale nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Mullick et al., "The cumate gene-switch: a system for regulated expression in mammalian cells", BMC Biotechnology, 6:43 (2006).
Nalla et al., "Automated splicing mutation analysis by information theory," Hum. Mutat., 25:334-342 (2005).
No et al., "Ecdysone-inducible gene expression in mammalian cells and transgenic mice," PNAS, 93(8):3346-3351 (1996).
Ohtsuka, "Lantibiotics: mode of action, biosynthesis and bioengineering," Curr Pharm Biotechnol, 10(2):244-51 (2009).
Patron, "DNA assembly for plant biology: techniques and tools," Curr Opinion Plant Biol., 19:14-9 (2014).
Sands et al., "Overview of Post Cohen-Boyer Methods for Single Segment Cloning and for Multisegment DNA Assembly," Curr Protoc Mol Biol., 113:3.26.1-3.26.20 (2016).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
West et al., "Molecular Dissection of Mammalian RNA Polymerase II Transcriptional Termination," Mol Cell. 29(5):600-10 (2008).
West et al., "Transcriptional Termination Enhances Protein Expression in Human Cells," Mol Cell.; 33(3-9); 354-364 (2009).
International Search Report and Written Opinion for International Application No. PCT/US2018/53608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/53671, dated Sep. 26, 2018, p. 1-12.
International Search Report and Written Opinion for International Application No. PCT/US2018/040519, dated Sep. 26, 2018, p. 1-8.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.

(56) References Cited

OTHER PUBLICATIONS

Final Office Action for U.S. Appl. No. 16/024,816 dated Nov. 26, 2018, p. 1-12.
International Search Report and Written Opinion for International Application No. PCT/US2019/023342 dated Jun. 6, 2019, p. 1-12.
First Office Action Interview Pilot Program Pre-Interview Communication for U.S. Appl. No. 16/360,404 dated Jul. 1, 2019, p. 1-27.
First Office Action Interview Pilot Program Pre-Interview Communication for U.S. Appl. No. 16/360,423 dated Jul. 1, 2019, p. 1-27.
International Search Report and Written Opinion for International Application No. PCT/US2018/053671, dated Nov. 23, 2018, p. 1-12.
International Search Report and Written Opinion for International Application No. PCT/US2019/030085, dated Jul. 23, 2019, p. 1-14.
NonFinal Office Action for U.S. Appl. No. 16/399,988, dated Jul. 31, 2019, p. 1-20.
International Search Report and Written Opinion for International Application No. PCT/US19/47135, dated Jun. 11, 2020, p. 1-15.
International Search Report and Written Opinion for International Application No. PCT/US2019/026836 dated Jul. 2, 2019, p. 1-10.
International Search Report and Written Opinion for International Application No. PCT/US2019/028821 dated Aug. 2, 2019, p. 1-14.
International Search Report and Written Opinion for Interational Application No. PCT/US2019/028883 dated Aug. 16, 2019, p. 1-12.
Pre-Interview First Office Action in U.S. Appl. No. 16/454,865, dated Aug. 16, 2019, p. 1-36.
Yoshioka, et al., "Development for a mono-promoter-driven CRISPR/CAS9 system in mammalian cells", Scientific Reports, Jul. 3, 2015, p. 1-8.
Remaut, et al., "Plasmid vectors for high-efficiency expression controlled by the PL promoter of coliphage lambda", Laboratory of Molecular Biology, Apr. 15, 1981, p. 81-93.
DuCoeur et al., "Control of Gene Expression in Eukaryotic Cells Using the Lac Repressor System," *Strategies* 5(3), pp. 70-72 (1992) (**).
Gossen et al., "Tight control of gene expression mammalian cells by tetracycline-Responsive promoters," *PNAS*, 89(12), pp. 5547-5551 (1992) (Washington, DC, US).
Wyborski et al., "Parameters Affecting the Use of the lac Repressor System in Eukaryotic Cells and Transgenic Animals," *Environ Mol Mutagen*, 28(4), pp. 447-58 (1996) (Hoboken, New Jersey, US).
Zhang et al., "Incredible site-directed recombination in mouse embryonic stem cells," *Nucleic Acids Research*, 24:543-548 (1996) (Oxford, England, UK).
Examination Search Report dated Jan. 31, 2023 in Canadian Application No. 3,108,892.
"How Confluent Are Your Cells? A Beginner's Guide to Measuring Cell Culture," *BiteSize Bio*, https://bitesizebio.com/63887/cell-confluency/, 8 pages (May 2022).

* cited by examiner

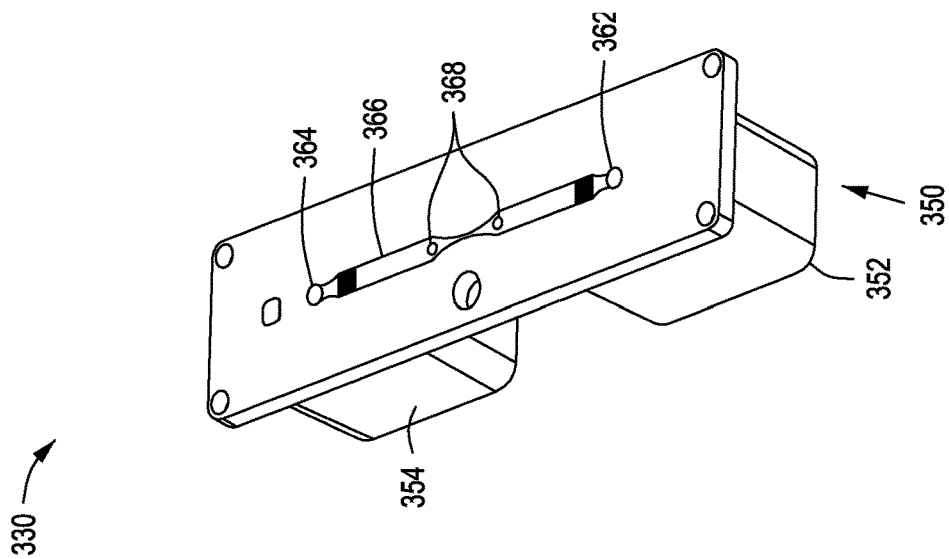
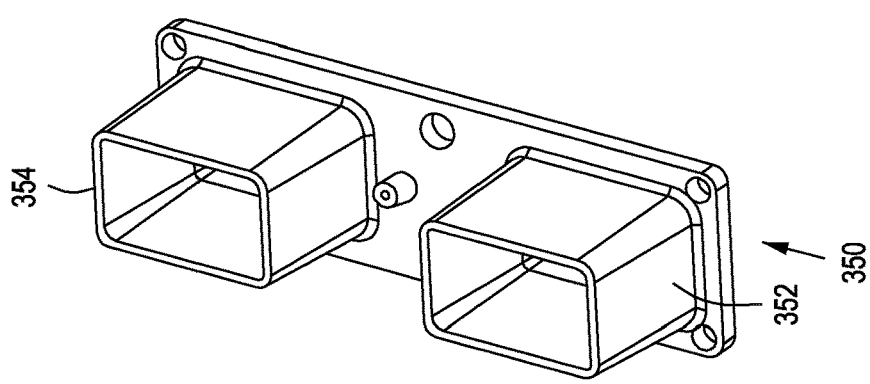
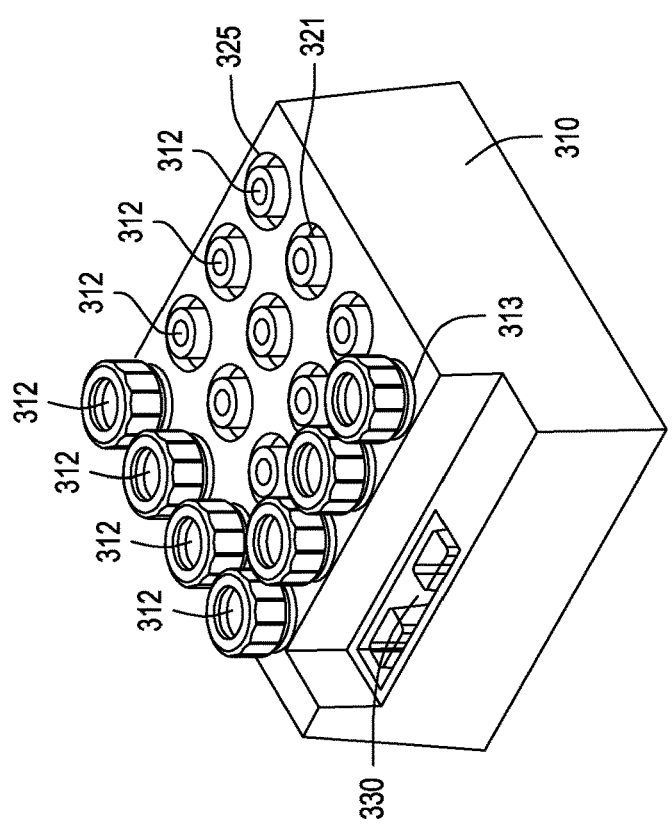
FIG. 3D
FIG. 3C
FIG. 3B

DETECTION OF NUCLEASE EDITED SEQUENCES IN AUTOMATED MODULES AND INSTRUMENTS

RELATED APPLICATIONS

This application claims priority to U.S. Provisional Application Nos. 62/724,851, filed 30 Aug. 2018; and 62/795,739, filed 23 Jan. 2019, both of which are incorporated by reference in their entirety for all purposes.

FIELD OF THE INVENTION

This invention relates to automated modules, instruments and methods for nucleic acid-guided nuclease editing and enrichment of live cells that have been edited.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the methods referenced herein do not constitute prior art under the applicable statutory provisions.

The ability to make precise, targeted changes to the genome of living cells has been a long-standing goal in biomedical research and development. Recently various nucleases have been identified that allow manipulation of gene sequence, and hence gene function. The nucleases include nucleic acid-guided nucleases, which enable researchers to generate permanent edits in live cells. Editing efficiencies in cell populations can be high: however, in pooled or multiplex formats there tends to be selective enrichment of cells that have not been edited due to the lack of the double-strand DNA breaks that occur during the editing process. Double-strand DNA breaks dramatically negatively impact cell viability thereby leading to the enhanced survival of unedited cells and making it difficult to identify edited cells. In addition, cells with edits that confer growth advantages or disadvantages can lead to skewed representations for different edits in the population.

There is thus a need in the art of nucleic acid-guided nuclease gene editing for improved methods for generating edits in cell populations and improved methods for enriching and selecting for the cells that have been edited. The present invention satisfies this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure provides methods, modules, and instruments for automated high-throughput enrichment for cells edited by a nucleic acid-guided nuclease. The methods take advantage of induction of editing at a specific point in the cell growth cycle, where one or both of the nuclease and the gRNA are under the control of an inducible promoter. Induction of editing when a cell culture reaches the stationary phase of growth (or shortly before a cell culture reaches a stationary phase of growth) overcomes growth bias from unedited cells, growth effects from differential editing rates, and growth bias resulting from fitness effects of different edits. Indeed, it has been determined that removing growth rate bias improves the observed editing efficiency by up to 3-4× or more over conventional methods.

Thus, presented herein is an embodiment comprising a method for performing enrichment of cells edited by a nucleic acid-guided nuclease the method comprising: providing transformed cells in growth medium where the cells comprise nucleic-acid guided nuclease editing components and where at least the gRNA is under the control of an inducible promoter; allowing the transformed cells to grow until the cells have grown for at least 60% of log phase; inducing transcription of the one or more nucleic-acid guided nuclease editing components; and allowing the cells to edit, and then to grow. In some aspects, the nucleic-acid guided nuclease editing components are provided to the cells on a single vector, and in some aspects, the cells are bacterial cells, yeast cells, or mammalian cells. In some aspects, the method further comprises after the second allowing step the step of rendering the cells electrocompetent and transforming the cells with a second round of nucleic acid guided nuclease editing components where at least the gRNA is under the control of an inducible promoter. In yet some aspects, the cells are grown until they have grown for at least 75% of log phase, 80% of log phase, 85% of log phase, 90% of log phase, 95% of log phase, or are in a stationary phase of growth before inducing transcription of the one or more nucleic-acid guided nuclease editing components.

In some aspects, the inducible promoter is a promoter that is activated upon an increase in temperature, and in some aspects, the inducible promoter is a pL promoter where transcription is induced by raising temperature of the cells to 42° C. In yet other aspects, the inducible promoter is a promoter that is activated upon adding an inducing moiety.

Other embodiments provide an automated stand-alone multi-module cell processing instrument for performing automated enrichment of cells edited by a nucleic acid-guided nuclease editing comprising: a receptacle for receiving cells; a receptacle for receiving nucleic acids comprising a coding sequence for a nuclease, a guide nucleic acid and a DNA donor sequence, wherein at least transcription of the guide nucleic acid is under the control of an inducible promoter; a first growth module for growing cells to be transformed; a filtration module for concentrating and rendering electrocompetent the grown cells; a transformation module for transforming the electrocompetent cells with the nucleic acids; a second growth module for growing transformed cells, wherein the second growth module comprises a vessel for growing cells; a spectrophotometer configured to monitor the growth of the transformed cells; and a temperature assembly to provide a temperature to induce the inducible promoter; a processor; and an automated liquid handling system to move liquids from the receptacle for receiving cells to the first growth module, from the first growth module to the filtration module, from the filtration module to the transformation module, from the receptacle for receiving nucleic acids to the transformation module, and from the transformation module to the second growth module according to a script run by the processor and without user intervention.

In some aspects, instead of a temperature-inducible promoter, the inducible promoter is induced by addition of an inducing agent supplied by the automated liquid handling system In some aspects the second growth module further comprises an alarm to alert a user that the cells have reached 60% of log phase or greater. In some aspects, the first growth module and the second growth module are the same growth module. In some aspects, the automated stand-alone multi-module cell processing instrument further comprises a housing, and/or a reagent cartridge. In some aspects, the transformation module comprises a flow-through electroporation device; and/or the first growth module comprises a rotating growth vial; and/or the second growth module comprises a rotating growth vial.

Additionally provided is a method for performing enrichment of cells edited by a nucleic acid-guided nuclease comprising: providing transformed cells in growth medium, wherein the cells comprise first nucleic-acid guided nuclease editing components, wherein at least a first gRNA is under the control of an inducible promoter; allowing the transformed cells to grow until the cells have grown for at least 60% of log phase; inducing transcription of the gRNA; allowing the cells to edit and then to grow to an optical density appropriate for transformation; and transforming the cells with second nucleic acid guided nuclease editing components wherein a second gRNA is under the control of an inducible promoter. In some aspects, the cells are grown for at least 75%, 85%, or 95% of log phase or the cells are grown until they reach a stationary phase of growth.

These aspects and other features and advantages of the invention are described below in more detail.

DETAILED DESCRIPTION

Figure 1A:
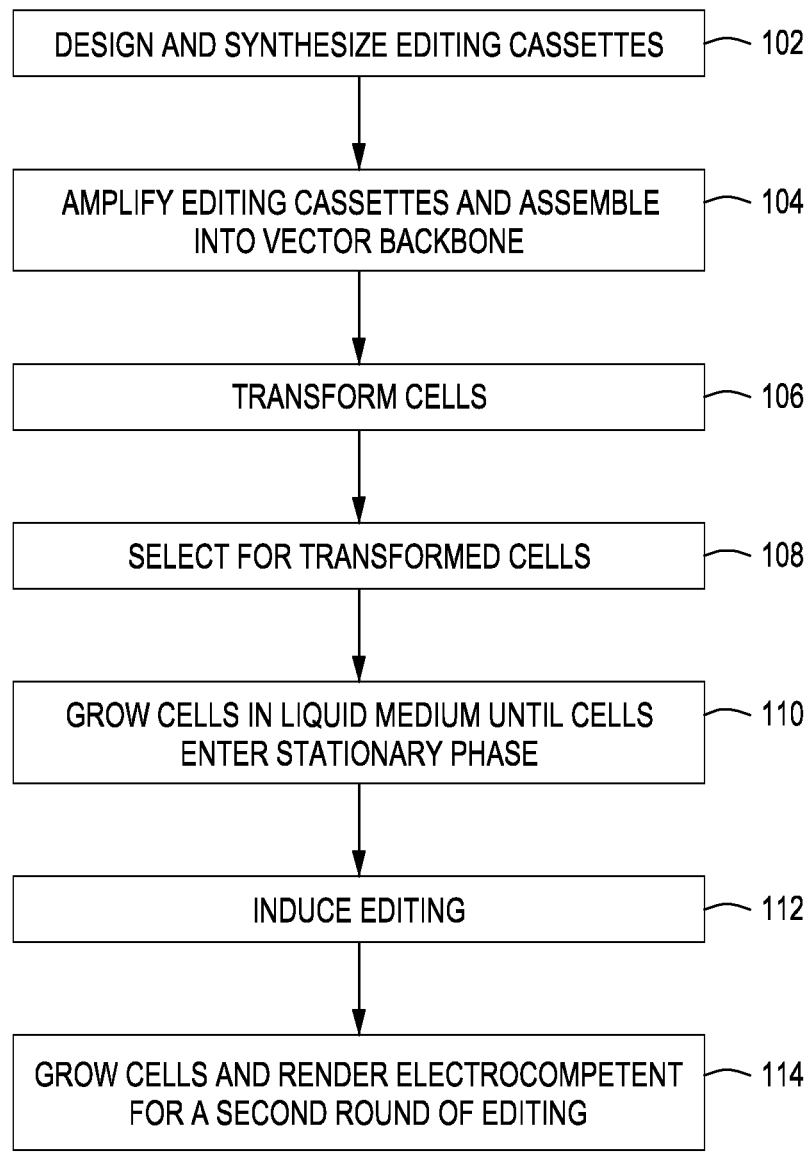
FIG. 1A is a simplified block diagram of methods for editing live cells via nucleic acid-guided nuclease editing in bulk liquid culture.

All of the functionalities described in connection with one embodiment are intended to be applicable to the additional embodiments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, biochemistry, biological emulsion generation, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* $3^{rd}$ Ed., W. H. Freeman Pub., New York, N.Y.; Berg et al. (2002) *Biochemistry*, $5^{th}$ Ed., W.H. Freeman Pub., New York, N.Y.; *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011), all of which are herein incorporated in their entirety by reference for all purposes. CRISPR-specific techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "an oligonucleotide" refers to one or more oligonucleotides, and reference to "an automated system" includes reference to equivalent steps and methods for use with the system known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of ordinary skill in the art that the present invention may be practiced without one or more of these specific details. In other instances, well-known features and procedures well known to those skilled in the art have not been described in order to avoid obscuring the invention.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

As used herein the term "donor DNA" or "donor nucleic acid" refers to a nucleic acid that is designed to introduce a DNA sequence modification (insertion, deletion, substitution) into a locus by homologous recombination using nucleic acid-guided nucleases. For homology-directed repair, the donor DNA must have sufficient homology to the regions flanking the "cut site" or site to be edited in the genomic target sequence. The length of the homology arm(s) will depend on, e.g., the type and size of the modification being made. In many instances and preferably, the donor DNA will have two regions of sequence homology (e.g., two homology arms) to the genomic target locus. Preferably, an "insert" region or "DNA sequence modification" region— the nucleic acid modification that one desires to be introduced into a genome target locus in a cell—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

As used herein, "enrichment" or "screening" refers to enriching for edited cells by culturing cells in liquid medium, growing cells until the cells reach stationary growth phase (e.g., the growth phase subsequent to the log or exponential growth phase), then inducing editing of the cells by inducing transcription of at least the gRNA and, in some embodiments, the nuclease as well.

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refers to one, some, or all of a nuclease, a guide nucleic acid, a donor nucleic acid, and, in bacteria, a recombination (e.g., recombineering) systems if required.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in the method herein the transcription of at least the gRNA is inducible and one or more other components of the nucleic acid-guided nuclease editing system is under the control of an inducible promoter.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, puromycin, hygromycin, blasticidin, and G418 may be employed. In other embodiments, selectable markers include, but are not limited to human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); rhamnose; and Cytidine deaminase (CD; selectable by Ara-C). "Selective medium" as used herein refers to cell growth medium to which has been added a chemical compound or biological moiety that selects for or against selectable markers.

The terms "target genomic DNA sequence", "target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The target sequence can be a genomic locus or extrachromosomal locus.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereto. Engine vectors also typically comprise a selectable marker. As used herein the phrase "editing vector" comprises at least two contiguously-linked editing cassettes, where each editing cassette comprises a coding sequence for a guide RNA (gRNA), a coding sequence for a donor nucleic acid, and an alteration to the target sequence that prevents nuclease binding at a PAM or spacer in the target sequence after editing has taken place. The editing vector may also comprise a selectable marker and/or a barcode. In some embodiments, the engine vector and editing vector may be combined; that is, the nucleic acid-guided nuclease system components on the engine vector may be found on the editing vector. Further, the engine and editing vectors comprise control sequences operably linked to, e.g., the nuclease coding sequence, recombineering system coding sequences (if present), donor nucleic acid, guide nucleic acid, and selectable marker(s).

Editing in Nucleic Acid-Guided Nuclease Genome Systems Generally

The present disclosure provides methods and instruments for nucleic acid-guided nuclease editing of live cells, and, in particular, high-throughput methods for improved enrichment of edited cells grown in bulk liquid culture. The compositions and methods described herein improve CRISPR editing systems in which nucleic acid-guided nucleases (e.g., RNA-guided nucleases) are used to edit specific target regions in an organism's genome. A nucleic acid-guided nuclease complexed with an appropriate synthetic guide nucleic acid in a cell can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby.

In general, a guide nucleic acid (e.g., gRNA) complexes with a compatible nucleic acid-guided nuclease and can then hybridize with a target sequence, thereby directing the nuclease to the target sequence. The gRNA may be encoded by a DNA sequence on a polynucleotide molecule such as a plasmid, linear construct, or the coding sequence may reside within an editing cassette and is under the control of an inducible promoter as described below.

A guide nucleic acid comprises a guide sequence, where the guide sequence is a polynucleotide sequence having sufficient complementarity with a target sequence to hybridize with the target sequence and direct sequence-specific binding of a complexed nucleic acid-guided nuclease to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20 nucleotides in length. Preferably the guide sequence is 10-30 or 15-20 nucleotides long, or 15, 16, 17, 18, 19, or 20 nucleotides in length.

In preferred embodiments, the guide nucleic acid is provided as a coding sequence in an editing cassette to be expressed from a plasmid or vector and comprises both the guide sequence and the scaffold sequence as a single transcript under the control of an inducible promoter. US Patents and Application describing various aspects of editing cassettes include U.S. Pat. No. 10,240,167, issued 26 Mar. 2019; U.S. Pat. No. 10,266,849, filed 23 Apr. 2019; U.S. Pat. No. 9,982,278, issued 29 May 2018; U.S. Pat. No. 10,351,877, issued 16 Jul. 2019; and U.S. Pat. No. 10,362,442, issued 30 Jul. 2019; and U.S. Ser. No. 16/275,439, filed 14 Feb. 2018; and Ser. No. 16/275,465, filed 14 Feb. 2019. The guide nucleic acid can be engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif PAM) sequence adjacent to the target sequence. The target sequence can be any genomic or episomic polynucleotide whether endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, a spacer, or "junk" DNA).

The target sequence is associated with a PAM, which is a short nucleotide sequence recognized by the gRNA/nuclease complex. The precise PAM sequence and length requirements for different nucleic acid-guided nucleases vary; however, PAMs typically are 2-7 base-pair sequences adjacent or in proximity to the target sequence and, depending on the nuclease, can be 5' or 3' to the target sequence. Engineering of the PAM-interacting domain of a nucleic acid-guided nuclease allows for alteration of PAM specificity, improved target site recognition fidelity, decreased target site recognition fidelity, or increased versatility of a nucleic acid-guided nuclease. In certain embodiments, the editing cassette provides donor DNA sequences that allow for genome editing of a target sequence including both a desired DNA change to a target sequence, e.g., the genomic DNA of a cell, and removal of, mutation of, or rendering inactive a proto-spacer mutation (PAM) region in the target sequence. Rendering the PAM at the target sequence inactive precludes additional editing of the cell genome at that target sequence, e.g., upon subsequent exposure to a nucleic acid-guided nuclease complexed with a synthetic guide nucleic acid in later rounds of editing. Thus, cells having the desired target sequence edit and an altered PAM can be selected using a nucleic acid-guided nuclease complexed with a synthetic guide nucleic acid complementary to the target sequence. Cells that did not undergo the first editing event will be cut rendering a double-stranded DNA break, and thus will not continue to be viable. The cells containing the desired target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a large background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the nucleic acid-guided nuclease editing system, a polynucleotide sequence encoding the nucleic acid-guided nuclease can be codon optimized for expression in particular cells, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of nucleic acid-guided nuclease to be employed depends on many factors, such as what type of edit is to be made in the target sequence and whether an appropriate PAM is located close to the desired target sequence. Nucleases of use in the methods described herein include but are not limited to Cas 9, Cas 12 (e.g., Cpf1), MAD2, MAD7, and other MADzymes. As with the guide nucleic acid, the nuclease may be and preferably is encoded by a DNA sequence on a vector (e.g., the engine vector) and may be and preferably is under the control of an inducible promoter. In some embodiments, the sequence encoding the nuclease is under the control of an inducible promoter, and the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter system.

Another component of the nucleic acid-guided nuclease system is the donor nucleic acid. The donor nucleic acid is on the same polynucleotide (e.g., editing cassette) as the guide nucleic acid and may be (but not necessarily) under the control of the same promoter as the guide nucleic acid (e.g., a single promoter driving the transcription of both the guide nucleic acid and the donor nucleic acid). The donor nucleic acid is designed to serve as a template for homologous recombination with a target sequence nicked or cleaved by the nucleic acid-guided nuclease as a part of the gRNA/nuclease complex. A donor nucleic acid polynucleotide may be of any suitable length, such as about or more than about 20, 25, 50, 75, 100, 150, 200, 500, or 1000 nucleotides in length. In certain preferred aspects, the donor nucleic acid can be provided as an oligonucleotide of between 20-300 nucleotides, more preferably between 50-250 nucleotides. The donor nucleic acid comprises a region that is complementary to a portion of the target sequence (e.g., a homology arm). When optimally aligned, the donor nucleic acid overlaps with (is complementary to) the target sequence by, e.g., about 20, 25, 30, 35, 40, 50, 60, 70, 80, 90 or more nucleotides. In many embodiments, the donor nucleic acid comprises two homology arms (regions complementary to the target sequence) flanking the mutation or difference between the donor nucleic acid and the target template. The donor nucleic acid comprises at least one mutation or alteration compared to the target sequence, such as an insertion, deletion, modification, or any combination thereof compared to the target sequence.

The donor nucleic acid may be and preferably is provided as a component in an editing cassette, where the editing cassette may be one of multiple editing cassettes inserted into a vector backbone. That is, there may be more than one, e.g., two, three, four, five or more individual editing cassettes inserted into an editing vector, where each guide nucleic acid/donor nucleic acid pair is under the control of separate different promoters, separate like promoters, or where all guide nucleic acid/donor nucleic acid pairs are under the control of a single promoter. See, e.g., U.S. Ser. No. 16/275,465, filed 14 Feb. 2019. As stated previously, the promoter driving transcription of the gRNAs is an inducible promoter. In some embodiments, transcription of the nuclease is also inducible, and in some embodiments, transcription of both the nuclease and gRNA are inducible. Inducible editing is advantageous in that cells can be grown for several to many cell doublings to a stationary growth phase (or nearly so) before editing is initiated, which increases the likelihood that cells with edits will survive. Editing tends to be toxic to the cells due to the double-strand DNA breaks made during editing. This toxicity results both in cell death in the edited cells as well as a lag in growth for the edited cells that do survive but must repair and recover following editing.

In addition to the donor nucleic acid, an editing cassette may comprise one or more primer sites. The primer sites can be used to amplify the editing cassettes and to assemble multiplexed editing cassettes by using oligonucleotide primers and bridging oligos; for example, if the primer sites flank one or more of the other components of the editing cassette.

Also, as described above, the donor nucleic acid may comprise—in addition to the at least one mutation relative to a target sequence—one or more PAM sequence alterations that mutate, delete or render inactive the PAM site in the target sequence. The PAM sequence alteration in the target sequence renders the PAM site "immune" to the nucleic acid-guided nuclease and protects the target sequence from further editing in subsequent rounds of editing if the same nuclease is used.

In addition, an editing cassette may comprise a barcode. A barcode is a unique DNA sequence that corresponds to the donor DNA sequence such that the barcode can identify the edit made to the corresponding target sequence. The barcode typically comprises four or more nucleotides. In some embodiments, the editing cassettes comprise a collection of donor nucleic acids representing, e.g., gene-wide or genome-wide libraries of donor nucleic acids. The library of editing cassettes are assembled into multiplex editing cassettes of at least two editing cassettes and then cloned into vector backbones where, e.g., each different donor nucleic acid is associated with a different barcode.

Additionally, in some embodiments, a vector encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The engine and editing vectors (or combined engine/editing single vector) comprise control sequences operably linked to the component sequences to be transcribed. As stated above, the promoters driving transcription of at least the gRNA and optionally one or more additional components of the nucleic acid-guided nuclease editing system is inducible. A number of gene regulation control systems have been developed for the controlled expression of genes in plant, microbe, and animal cells, including mammalian cells, including the pL promoter (induced by heat inactivation of the CI857 repressor), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, CA); Bujard and Gossen, PNAS, 89(12):5547-5551 (1992)), the Lac Switch Inducible system (Wyborski et al., Environ Mol Mutagen, 28(4):447-58 (1996); DuCoeur et al., Strategies 5(3):70-72 (1992); U.S. Pat. No. 4,833,080), the ecdysone-inducible gene expression system (No et al., PNAS, 93(8): 3346-3351 (1996)), the cumate gene-switch system (Mullick et al., BMC Biotechnology, 6:43 (2006)), and the tamoxifen-inducible gene expression (Zhang et al., Nucleic Acids Research, 24:543-548 (1996)) as well as others.

The present compositions and methods make use of editing cassettes such as the editing cassettes described in US Patents and Application describing various aspects of editing cassettes include U.S. Pat. No. 10,240,167, issued 26 Mar. 2019; U.S. Pat. No. 10,266,849, filed 23 Apr. 2019; U.S. Pat. No. 9,982,278, issued 29 May 2018; U.S. Pat. No. 10,351,877, issued 16 Jul. 2019; and U.S. Pat. No. 10,362,442, issued 30 Jul. 2019; and U.S. Ser. No. 16/275,439, filed 14 Feb. 2018; and Ser. No. 16/275,465, filed 14 Feb. 2019. Each editing cassette comprises a gRNA, a donor DNA, and a PAM or spacer mutation; thus, e.g., a two-cassette multiplex editing cassette comprises a first gRNA, a first donor DNA, and a first PAM or spacer mutation, and at least a second gRNA, at least a second donor DNA, and at least a second PAM or spacer mutation. See, e.g., U.S. Ser. No. 16/275,465, filed 14 Feb. 2019. In some embodiments, a single promoter may drive transcription of both the first and second gRNAs and both the first and second donor DNAs, and in some embodiments, separate promoters may drive transcription of the first gRNA and first donor DNA, and transcription of the second gRNA and second donor DNA. In addition, the multiplex editing cassettes may comprise nucleic acid elements between the editing cassettes with, e.g., primer sequences, bridging oligonucleotides, and other "cassette-connecting" sequence elements that allow for the assembly of the multiplex editing cassettes. The synthesis and assembly approach for multiplex editing cassettes lends itself to "tunable" incorporation of different edits at different frequencies based on the representation of each gRNA/donor DNA cassette in a pool of synthesized editing cassettes.

FIG. 1A shows a simplified flow chart for exemplary method 100 for enriching for edited cells. Looking at FIG. 1A, method 100 begins by designing and synthesizing editing cassettes 102. As described above, each editing cassette comprises a gRNA, a donor DNA, and a PAM or spacer mutation. Once the individual editing cassettes have been synthesized, the individual editing cassettes may be "linked" or "assembled" together and are amplified and assembled into editing vector backbones 104 such that the editing cassette is positioned 3' of an inducible promoter. The editing vectors comprising the editing cassettes are then used to transform cells 106 thereby creating a library of transformed cells. In addition to the vectors comprising the assembled editing cassettes, the cells may be transformed simultaneously with a separate engine vector comprising a coding sequence for a nuclease. Alternatively, the cells may already be expressing the nuclease (e.g., the cells may have already been transformed with an engine vector or the coding sequence for the nuclease may be stably integrated into the cellular genome) such that only the editing vector needs to be transformed into the cells; or the cells may be transformed with a single vector comprising all components required to perform nucleic acid-guided nuclease genome editing (e.g., all of the nuclease and an editing cassette), which is advantageous when employing curing and recursive rounds of editing.

A variety of delivery systems may be used to introduce (e.g., transform or transfect) nucleic acid-guided nuclease editing system components into a host cell 108. These delivery systems include the use of yeast systems, lipofection systems, microinjection systems, biolistic systems, virosomes, liposomes, immunoliposomes, polycations, lipid: nucleic acid conjugates, virions, artificial virions, viral vectors, electroporation, cell permeable peptides, nanoparticles, nanowires, exosomes. Alternatively, molecular trojan horse liposomes may be used to deliver nucleic acid-guided nuclease components across the blood brain barrier. Of particular interest is the use of electroporation, particularly flow-through electroporation (either as a stand-alone instrument or as a module in an automated multi-module system) as described in, e.g., Ser. No. 16/147,120, filed 28 Sep. 2018; Ser. No. 16/147,353 filed 28 Sep. 2018; Ser. No. 16/147,865 filed 30 Sep. 2018; Ser. No. 16/426,310, filed 30 May 2019; and Ser. No. 16/147,871, filed 30 Sep. 2018. If the screening/selection module is one module in an automated multi-module cell editing system, the cells are likely transformed in an automated cell transformation module.

Once transformed 106, the cells can then be subjected to selection using a selectable marker 108. Selectable markers are employed to select for cells that have received both the engine and editing vectors, or for cells that have been transformed with a single, combined engine and editing vector. Commonly used selectable markers include drug selectable markers such as ampicillin/carbenicillin, kanamycin, chloramphenicol, erythromycin, tetracycline, gentamicin, bleomycin, streptomycin, rhamnose, puromycin, hygromycin, blasticidin, and G418.

Once cells that have been properly transformed are selected 108, the next step in method 100 is to grow cells in liquid medium until the cells enter (or are close to entering) the stationary phase of growth. Once the cells are in stationary phase 110 (or nearly so), editing is induced 112 in the cells by induction of transcription of at least the gRNA and preferably the nuclease as well. Once editing is induced 112, the cells can be grown, rendered electrocompetent, and subjected to another round of editing 114.

Figure 1B:
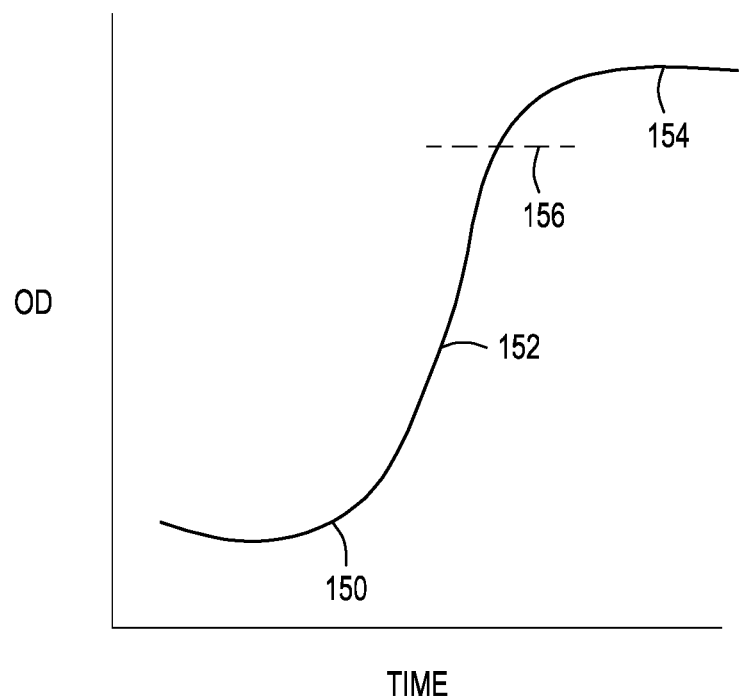
FIG. 1B depicts a typical growth curve for cells in culture.

FIG. 1B depicts a typical growth curve 160 for cells in culture (optical density versus time). Initially there is a lag phase 150, then the cells enter log phase 152 where they grow quickly, and finally the cells reach stationary phase 154 where the cells are no longer dividing. The present methods employ inducing transcription of at least the gRNA (and optionally the nuclease as well) at timepoint 156 or later when the cells are in the stationary phase of growth or nearly so; that is, the cells are induced at a timepoint at least 60% into the log phase of growth, or at least 65% into the log phase of growth, or at least 70% into the log phase of growth, or at least 71, 72, 73, 74, 75, 76, 77, 78, 79, 80, 81, 82, 83, 84, 85, 86, 87, 88, 89, 90, 91, 92, 93, 94, 95, 96, 79, 98, or 99% into the log phase of growth, and at any time during the stationary phase of growth.

Figure 2:
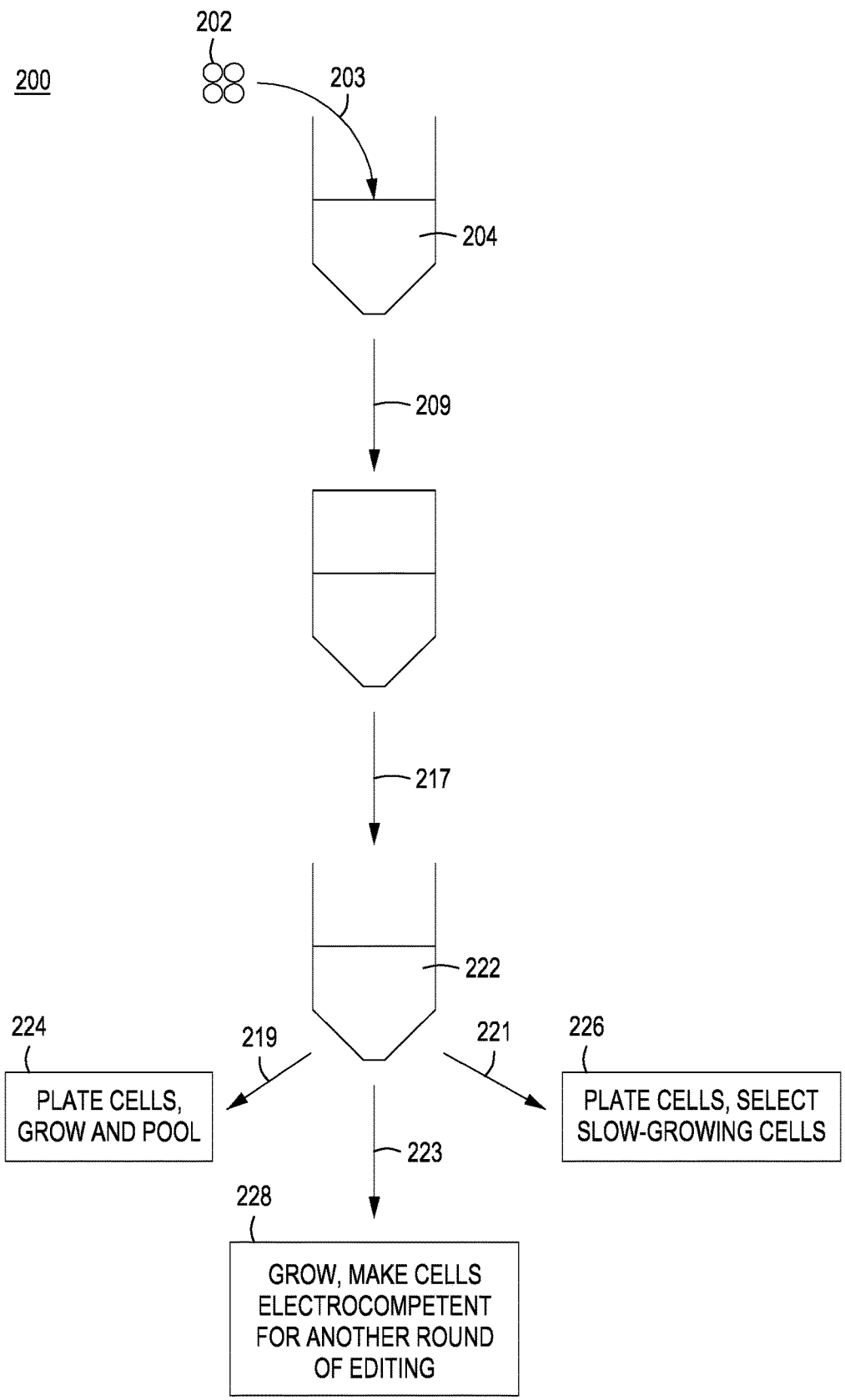
FIG. 2 is a graphic depiction of methods for growing, editing, enriching, and screening for edited cells in a population of cells.

FIG. 2 depicts an exemplary protocol for performing nucleic acid-guided nuclease genome editing. FIG. 2 depicts the protocols shown in FIG. 1A for editing cells. First, a library or collection of editing vectors 202 (editing vectors each comprising an editing cassette with the gRNA under control of an inducible promoter) is introduced 203 (e.g., electroporated) into cultured cells 204 that comprise a coding sequence for a nuclease under the control of a constitutive or inducible promoter (preferably an inducible promoter), contained 1) on an "engine plasmid" (most often along with a selectable marker) that has already been transformed into the cells; 2) integrated into the genome of the cells being transformed; or 3) the coding sequence for the nuclease may be located on the editing vector. The editing vectors 202 comprise a donor DNA, a PAM or spacer-altering sequence (most often a sequence that disables the PAM at the target site in the genome), a coding sequence for a gRNA under the control of an inducible promoter, and a selectable marker.

At step 209, cells are grown until they reach stationary phase, or nearly so. Once the cells reach the stationary phase, editing is induced 217 (e.g., where transcription of the gRNA or and optionally the nuclease is induced) and the cells in the culture 222 are edited and then allowed to recover from editing. Once recovered, the cells can be plated 219, grown and pooled 224. Alternatively, the cells from culture 222 can be plated 221, and slow-growing colonies are selected 226 (e.g., cherry-picking of small colonies). In yet another alternative, the cells can be retained in liquid culture, grown to an appropriate OD, rendered electrocompetent, and subjected to another round of editing 228. This method of enrichment of edited cells is particularly desirable as it may be performed in a high throughput manner and does not require plating cells and is automatable. Induction at step 217 can take place by, e.g., using a pL promoter system where the pL promoter is induced by raising the temperature of the cells in the medium 216 to 42° C. for, e.g., one to many hours to induce expression of the nuclease and gRNA for cutting and editing. Once editing has been induced and allowed to proceed for a desired period of time, the temperature of the culture 222 is returned to 30° C.

In one method 221, the cells from the bulk liquid culture are plated and the slow-growing colonies are selected 226. In edited cells, cell viability is compromised in the period after editing is induced. The selection method shown in FIG. 2 (e.g., selecting slow growing colonies 221) takes advantage of the growth lag in colonies of edited cells to identify edited cells. In some embodiments, the colony size of the edited cells is 20% smaller than colonies of non-edited cells. In some aspects the colony size of the edited cells is 30%, 40%, 50%, 60%, 70%, 80% or 90% smaller than the colonies of non-edited cells. In many embodiments, the colony size of the edited cells is 30-80% smaller than colonies of non-edited cells, and in some embodiments, the colony size of the edited cells is 40-70% smaller than colonies of non-edited cells.

While the method for screening for edited cells using cell growth as a proxy for editing has been described in the context of measuring colony size of cell colonies on an agar plate, the optical density (OD) of growing cell colonies, such as in a microtiter plate or in a series of tubes may be measured instead. Moreover, other cell growth parameters can be measured in addition to or instead of cell colony size or OD. For example, spectroscopy using visible, UV, or near infrared (NIR) light allows monitoring the concentration of nutrients and/or wastes in the cell culture. Additionally, spectroscopic measurements may be used to quantify multiple chemical species simultaneously. Nonsymmetric chemical species may be quantified by identification of characteristic absorbance features in the NIR. Conversely, symmetric chemical species can be readily quantified using Raman spectroscopy. Many critical metabolites, such as glucose, glutamine, ammonia, and lactate have distinct spectral features in the IR, such that they may be easily quantified. The amount and frequencies of light absorbed by the sample can be correlated to the type and concentration of chemical species present in the sample. Each of these measurement types provides specific advantages. FT-NIR provides the greatest light penetration depth and so can be used for thicker sample so that they provide a higher degree of light scattering. FT-mid-IR (MIR) provides information that is more easily discernible as being specific for certain analytes as these wavelengths are closer to the fundamental IR absorptions. FT-Raman is advantageous when the interference due to water is to be minimized. Other spectral properties can be measured via, e.g., dielectric impedance spectroscopy, visibly fluorescence, fluorescence polarization, or luminescence. Additionally, sensors for measuring, e.g., dissolved oxygen, carbon dioxide, pH, and/or conductivity may be used to assess the rate of cell growth. For additional methods and materials on selection or cherry-picking edited cells, see, U.S. Ser. No. 16/454,865, filed 26 Jun. 2019.

Automated Systems to Perform Nucleic Acid-Guided Nuclease Editing

Figure 3A:
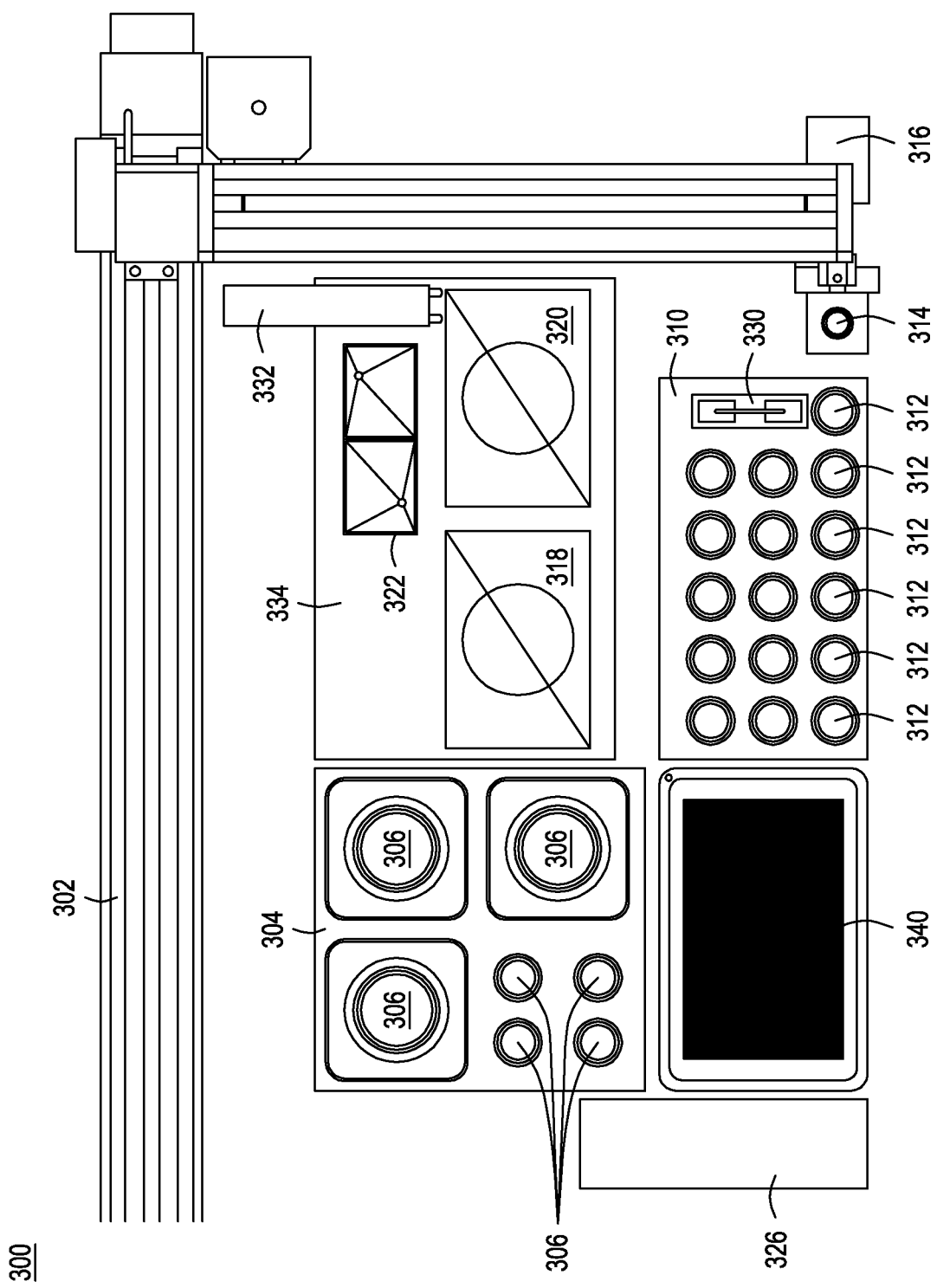
FIGS. 3A-3P depict an automated multi-module system and other modules thereof with which the enrichment/selection modules may be used.

FIG. 3A depicts an exemplary automated multi-module cell processing instrument 300 to, e.g., perform one of the exemplary workflows described above, as well as additional exemplary modules. Illustrated is a gantry 302, providing an automated mechanical motion system (actuator) (not shown) that supplies XYZ axis motion control to, e.g., modules of the automated multi-module cell processing instrument 300, including, e.g., an air displacement pipette 332. In some automated multi-module cell processing instruments, the air displacement pipettor is moved by a gantry and the various modules and reagent cartridges remain stationary; however, in other embodiments, the pipetting system may stay stationary while the various modules are moved. Also included in the automated multi-module cell processing instrument 300 is wash or reagent cartridge 304, comprising reservoirs 306. As described below in respect to FIG. 3B, wash or reagent cartridge 304 may be configured to accommodate large tubes, for example, wash solutions, or solutions that are used often throughout an iterative process. In one example, wash or reagent cartridge 304 may be configured to remain in place when two or more reagent cartridges 310 are sequentially used and replaced. Although reagent cartridge 310 and wash or reagent cartridge 304 are shown in FIG. 3A as separate cartridges, the contents of wash cartridge 304 may be incorporated into reagent cartridge 310.

The exemplary automated multi-module cell processing instrument 300 of FIG. 3A further comprises a cell growth module 334. In the embodiment illustrated in FIG. 3A, the cell growth module 334 comprises two cell growth vials 318, 320 (described in greater detail below with relation to FIG. 3E) as well as a cell concentration module 322 as described in more detail in relation to FIGS. 3J-3P. In alternative embodiments, the cell concentration module 322 may be separate from cell growth module 334, e.g., in a separate, dedicated module. Also illustrated as part of the automated multi-module cell processing instrument 300 of FIG. 3A is enrichment/selection module 340, served by, e.g., air displacement pipettor 332. Also seen are a waste repository 326, and a nucleic acid assembly/desalting module 314 comprising a reaction chamber or tube receptacle (not shown) and further comprising a magnet 316 to allow for purification of nucleic acids using, e.g., magnetic solid phase reversible immobilization (SPRI) beads (Applied Biological Materials Inc., Richmond, BC). The reagent cartridge, transformation module, and cell growth module are described in greater detail below. For a detailed description of automated multi-module cell processing instruments see U.S. Pat. No. 10,253,316, filed 30 Jun. 2018; U.S. Pat. No. 10,329,559, filed 7 Feb. 2019; and U.S. Pat. No. 10,323,242, filed 7 Feb. 2019; and U.S. Ser. No. 16/412,175, filed 14 May 2019; Ser. No. 16/412,195, filed 14 May 2019; and Ser. No. 16/423,289, filed 28 May 2019, all of which are herein incorporated by reference in their entirety.

FIG. 3B depicts an exemplary combination reagent cartridge and electroporation device 310 ("cartridge") that may be used in an automated multi-module cell processing instrument along with the screening/selection module. In certain embodiments the material used to fabricate the cartridge is thermally-conductive, as in certain embodiments the cartridge 310 contacts a thermal device (not shown), such as a Peltier device or thermoelectric cooler, that heats or cools reagents in the reagent receptacles or reservoirs 312. Reagent receptacles or reservoirs 312 may be receptacles into which individual tubes of reagents are inserted as shown in FIG. 3B, or the reagent receptacles may hold the reagents without inserted tubes. Additionally, the receptacles in a reagent cartridge may be configured for any combination of tubes, co-joined tubes, and direct-fill of reagents.

In one embodiment, the reagent receptacles or reservoirs 312 of reagent cartridge 310 are configured to hold various size tubes, including, e.g., 250 ml tubes, 25 ml tubes, 10 ml tubes, 5 ml tubes, and Eppendorf or microcentrifuge tubes. In yet another embodiment, all receptacles may be configured to hold the same size tube, e.g., 5 ml tubes, and reservoir inserts may be used to accommodate smaller tubes in the reagent reservoir (not shown). In yet another embodiment—particularly in an embodiment where the reagent cartridge is disposable—the reagent reservoirs hold reagents without inserted tubes. In this disposable embodiment, the reagent cartridge may be part of a kit, where the reagent cartridge is pre-filled with reagents and the receptacles or reservoirs sealed with, e.g., foil, heat seal acrylic or the like and presented to a consumer where the reagent cartridge can then be used in an automated multi-module cell processing instrument. As one skilled in the art will appreciate given the present disclosure, the reagents contained in the reagent cartridge will vary depending on workflow; that is, the reagents will vary depending on the processes to which the cells are subjected in the automated multi-module cell processing instrument.

Reagents such as cell samples, enzymes, buffers, nucleic acid vectors, editing cassettes, proteins or peptides, reaction components (such as, e.g., $MgCl_2$, dNTPs, nucleic acid assembly reagents, gap repair reagents, and the like), wash solutions, ethanol, and magnetic beads for nucleic acid purification and isolation, etc. may be positioned in the reagent cartridge at a known position. In some embodiments of cartridge 310, the cartridge comprises a script (not shown) readable by a processor (not shown) for dispensing the reagents. Also, the cartridge 310 as one component in an automated multi-module cell processing instrument may comprise a script specifying two, three, four, five, ten or more processes to be performed by the automated multi-module cell processing instrument. In certain embodiments, the reagent cartridge is disposable and is pre-packaged with reagents tailored to performing specific cell processing protocols, e.g., genome editing or protein production. Because the reagent cartridge contents vary while components/modules of the automated multi-module cell processing instrument or system may not, the script associated with a particular reagent cartridge matches the reagents used and cell processes performed. Thus, e.g., reagent cartridges may be pre-packaged with reagents for genome editing and a script that specifies the process steps for performing genome editing in an automated multi-module cell processing instrument, or, e.g., reagents for protein expression and a script that specifies the process steps for performing protein expression in an automated multi-module cell processing instrument.

For example, the reagent cartridge may comprise a script to pipette competent cells from a reservoir, transfer the cells to a transformation module (such as flow through electroporation device 330 in reagent cartridge 310), pipette a nucleic acid solution comprising a vector with expression cassette from another reservoir in the reagent cartridge, transfer the nucleic acid solution to the transformation module, initiate the transformation process for a specified time, then move the transformed cells to yet another reservoir in the reagent cassette or to another module such as a cell growth module in the automated multi-module cell processing instrument. In another example, the reagent cartridge may comprise a script to transfer a nucleic acid solution comprising a vector from a reservoir in the reagent cassette, nucleic acid solution comprising editing oligonucleotide cassettes in a reservoir in the reagent cassette, and a nucleic acid assembly mix from another reservoir to the nucleic acid assembly/desalting module (314 of FIG. 3A). The script may also specify process steps performed by other modules in the automated multi-module cell processing instrument. For example, the script may specify that the nucleic acid assembly/desalting reservoir be heated to 50° C. for 30 min to generate an assembled product; and desalting and resuspension of the assembled product via magnetic bead-based nucleic acid purification involving a series of pipette transfers and mixing of magnetic beads, ethanol wash, and buffer.

As described in relation to FIGS. 3C and 3D below, the exemplary reagent cartridges 310 for use in the automated multi-module cell processing instruments may include one or more electroporation devices 330, preferably flow-through electroporation devices. Electroporation is a widely-used method for permeabilization of cell membranes that works by temporarily generating pores in the cell membranes with electrical stimulation. Applications of electroporation include the delivery of DNA, RNA, siRNA, peptides, proteins, antibodies, drugs or other substances to a variety of cells such as mammalian cells (including human cells), plant cells, archea, yeasts, other eukaryotic cells, bacteria, and other cell types. Electrical stimulation may also be used for cell fusion in the production of hybridomas or other fused cells.

During a typical electroporation procedure, cells are suspended in a buffer or medium that is favorable for cell survival. For bacterial cell electroporation, low conductance mediums, such as water, glycerol solutions and the like, are often used to reduce the heat production by transient high current. In traditional electroporation devices, the cells and material to be electroporated into the cells (collectively "the cell sample") are placed in a cuvette embedded with two flat electrodes for electrical discharge. For example, Bio-Rad (Hercules, CA) makes the GENE PULSER XCELL™ line of products to electroporate cells in cuvettes. Traditionally, electroporation requires high field strength; however, the flow-through electroporation devices included in the reagent cartridges such as those shown in FIGS. 3B-3D achieve high efficiency cell electroporation with low toxicity. The reagent cartridges of the disclosure allow for particularly easy integration with robotic liquid handling instrumentation that is typically used in automated instruments and systems such as air displacement pipettors. Such automated instrumentation includes, but is not limited to, off-the-shelf automated liquid handling systems from Tecan (Mannedorf, Switzerland), Hamilton (Reno, NV), Beckman Coulter (Fort Collins, CO), etc. as described above.

FIGS. 3C and 3D are top perspective and bottom perspective views, respectively, of an exemplary flow-through electroporation device 350 that may be part of reagent cartridge 300 in FIG. 3B or may be contained in a separate module (e.g., a transformation/transfection module). FIG. 3C depicts a flow-through electroporation unit 350. The flow-through electroporation unit 350 has wells that define cell sample inlets 352 and cell sample outlets 354. FIG. 3D is a bottom perspective view of the flow-through electroporation device 350 of FIG. 3C. An inlet well 352 and an outlet well 354 can be seen in this view. Also seen in FIG. 3D are the bottom of an inlet 362 corresponding to well 352, the bottom of an outlet 364 corresponding to the outlet well 354, the bottom of a defined flow channel 366 and the bottom of two electrodes 368 on either side of flow channel 366. Additionally, flow-through electroporation devices may comprise push-pull pneumatic means to allow multi-pass electroporation procedures; that is, cells to be electroporated may be "pulled" from the inlet toward the outlet for one pass of electroporation, then be "pushed" from the outlet end of the flow-through electroporation device toward the inlet end to pass between the electrodes again for another pass of electroporation. This process may be repeated one to many times. For details of flow-through electroporation devices useful in automated multi-module cell processing instrumentation, see U.S. Ser. No. 16/147,120, filed 28 Sep. 2018; Ser. No. 16/147,353, filed 28 Sep. 2018; Ser. No. 16/147,865, filed 30 Sep. 2018; and Ser. No. 16/147,871, filed 30 Sep. 2018 all of which are herein incorporated by reference in their entirety. Further, other embodiments of the reagent cartridge may provide or accommodate electroporation devices that are not configured as flow-through devices, such as those described in U.S. Ser. No. 16/109,156 filed 22 Aug. 2018.

Figure 3E:
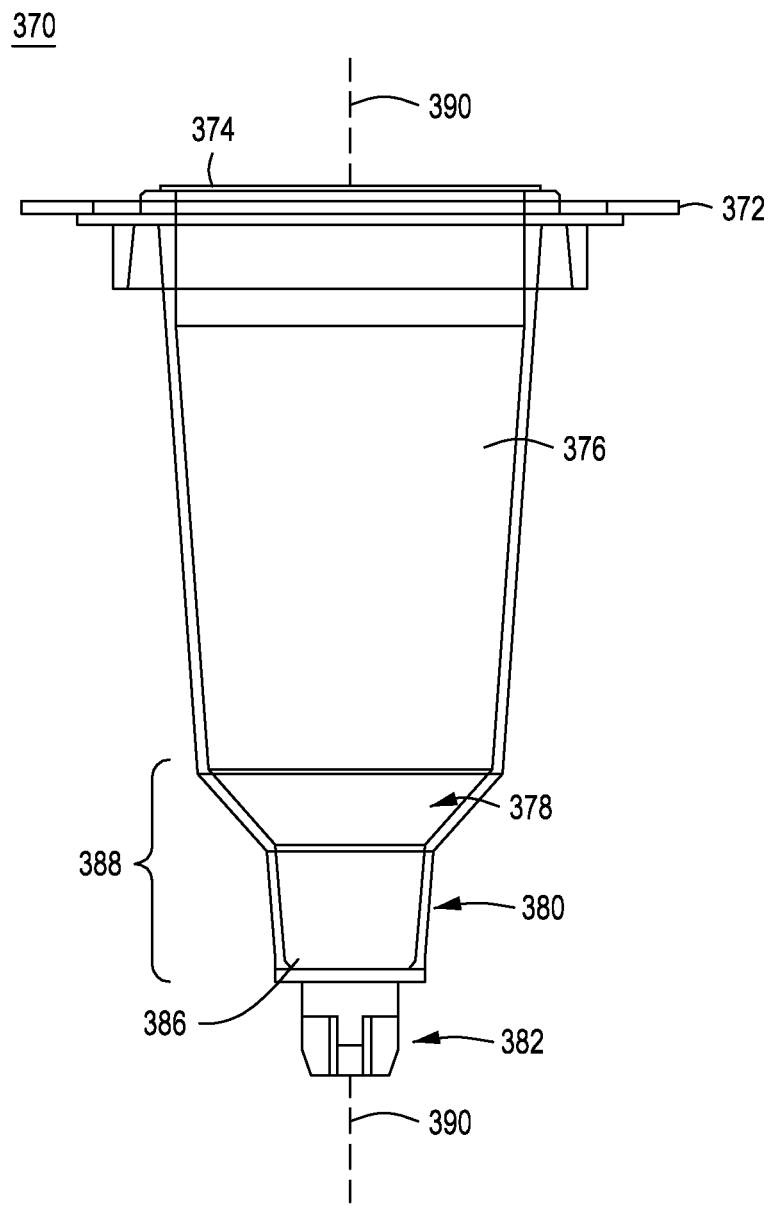

FIG. 3E depicts one embodiment of a growth vial that may be used with a cell growth module that is part of an automated multi-module cell processing instrument or system such as that shown in FIG. 3A. In one embodiment, the growth vial constantly measures the optical density of a growing cell culture. One advantage of the cell growth module is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 or so on minutes. Alternatively, OD can be measured at specific time intervals early in the cell growth cycle, and continuously after the OD of the cell culture reaches a set point OD. The cell growth module is controlled by a processor, which can be programmed to measure OD constantly or at intervals as defined by a user. A script on, e.g., the reagent cartridge(s) may also specify the frequency for reading OD, as well as the target OD and target time. Additionally, a user manually can set a target time at which the user desires the cell culture hit a target OD. To accomplish reaching the target OD at the target time, the processor measures the OD of the growing cells, calculates the cell growth rate in real time, and predicts the time the target OD will be reached. The processor then automatically adjusts the temperature of the cell growth vial (and the cell culture) as needed. Lower temperatures slow growth, and higher temperatures increase growth.

In the growth vial embodiment depicted in FIG. 3E, the growth vial 370 is a transparent container having an open end 374 for receiving liquid media and cells, a central vial region 376 that defines the primary container for growing cells, a tapered-to-constricted region 388 defining at least one light path 380, a closed end 386, and a drive engagement mechanism 382. The growth vial has a central longitudinal axis 390 around which the vial rotates, and the light path 380 is generally perpendicular to the longitudinal axis of the vial. The first light path 380 is positioned in the lower constricted portion of the tapered-to-constricted region 388. Optionally, some embodiments of the growth vial 370 have a second light path 378 in the tapered region of the tapered-to-constricted region 388. Both light paths in this embodiment are positioned in a region of the growth vial that is constantly filled with the cell culture (cells+growth media), and are not affected by the rotational speed of the growth vial. The first light path 380 is shorter than the second light path 378 allowing for sensitive measurement of OD values when the OD values of the cell culture in the vial are at a high level (e.g., later in the cell growth process), whereas the second light path 378 allows for sensitive measurement of OD values when the OD values of the cell culture in the vial are at a lower level (e.g., earlier in the cell growth process). The drive engagement mechanism 382 engages with a motor (not shown) to rotate the vial. The volume of the rotating growth vial may be from 5 mL to 250 mL, or from 10 mL to 200 mL, or from 15 mL to 150 mL or from 20 mL to 100 mL. For initial growth of cells before transcription, the volume of the rotating growth vial generally is on the lower side, e.g., 5 mL to 50 mL, and for growth and induction of editing, the volume of the rotating growth vial generally is on the higher side, e.g., 50 mL to 250 mL.

The growth vial 370 may be reusable, or preferably, the growth vial—like the reagent cartridge—is consumable. In some embodiments, the growth vial is consumable and is presented to a user pre-filled with growth medium, where the vial is sealed at the open end 374 with a foil seal.

The rotating growth vial can be used to grow the cells before transformation, but also can be used for the bulk culture growth and for induction of editing as the rotating growth vial provides the tools needed for cell growth, cell growth monitoring, induction of editing, and is serviced by a liquid handling system that can add culture medium or induction factors. Alternatively, the bulk culture growth and induction of editing can be done in a flask or other vessel, including test tubes, microtubes, or wells in 12-, 24-, 96-, and 128-well plates. The volume of the culture can range from 200 µL to 250 mL.

The exemplary automated multi-module cell processing instrument 300 of FIG. 3A also comprises an optional nucleic acid assembly module. The nucleic acid assembly module 314 is configured to perform, e.g., an isothermal nucleic acid assembly. An isothermal nucleic acid assembly joins multiple DNA fragments (such as single individual editing cassettes or multiple individual editing cassettes and a vector backbone) in a single, isothermal reaction, requiring few components and process manipulations. For example, an isothermal nucleic acid assembly can combine simultaneously up to 20 or more nucleic acid fragments (such as individual editing cassettes) based on sequence identity. The assembly method requires that the nucleic acids to be assembled comprise at least a 15-base overlap with adjacent nucleic acid fragments. The fragments are mixed with a cocktail of three enzymes—an exonuclease, a polymerase, and a ligase—along with buffer components. Because the process is isothermal and can be performed in a 1-step or 2-step method using a single reaction vessel, the isothermal nucleic acid assembly method is suited for use in an automated multi-module cell processing instrument. The 1-step method allows for the assembly of up to five different fragments using a single step isothermal process. The fragments and the master mix of enzymes are combined and incubated at 50° C. for up to one hour. For the creation of more complex constructs or for incorporating fragments from 100 bp up to 10 kb, typically the 2-step method is used, where the 2-step reaction requires two separate additions of master mix; one for the exonuclease and annealing step and a second for the polymerase and ligation steps.

In an embodiment of the exemplary automated multi-module cell processing instrument 300 of FIG. 3A, aliquots of a vector backbone, two or more individual editing cassettes to be inserted into the vector, and the nucleic acid assembly mix may be retrieved from three of the sixteen reagent reservoirs 312 disposed within reagent cartridge 310. The vector, editing cassettes, and reaction mix are combined in a reaction chamber or tube located in a tube receptacle (not shown) in the nucleic acid assembly module, and the module is heated to 50° C. After the nucleic acid assembly reaction has taken place, magnetic beads may be retrieved from one of the reagent reservoirs 312 disposed within reagent cartridge 310 and added to the nucleic acid assembly mix in the reaction chamber of the nucleic acid module 314. As seen in FIG. 3A, magnet 316, such as a solenoid magnet, is adjacent or proximal to the nucleic acid assembly module 314. Once the magnetic beads are added to the nucleic acid assembly reaction the nucleic acid product binds the magnetic beads, and after a period of incubation magnet 316 is engaged, isolating the magnetic beads coupled to the nucleic acids in the reaction chamber. The reaction solution (supernatant) in the nucleic acid assembly module 314 can be removed by air displacement pipettor 332, and a wash solution and/or ethanol may be pipetted from a reagent reservoir 312 in reagent cartridge 310, or from a wash solution reservoir 306 in wash cartridge 304 and used to wash the nucleic acids coupled to the beads. The magnet may be disengaged while the beads and coupled nucleic acids are being washed, then the magnet would be re-engaged to remove the wash solution from the nucleic acid assembly module. Alternatively, the magnet may not be disengaged while the beads and coupled nucleic acids are washed. The de-salted assembled vector+editing cassettes may then be moved to, e.g., the flow-through electroporation device (transformation/transfection module) as described in relation to FIGS. 3B through 3D.

Figure 3F:
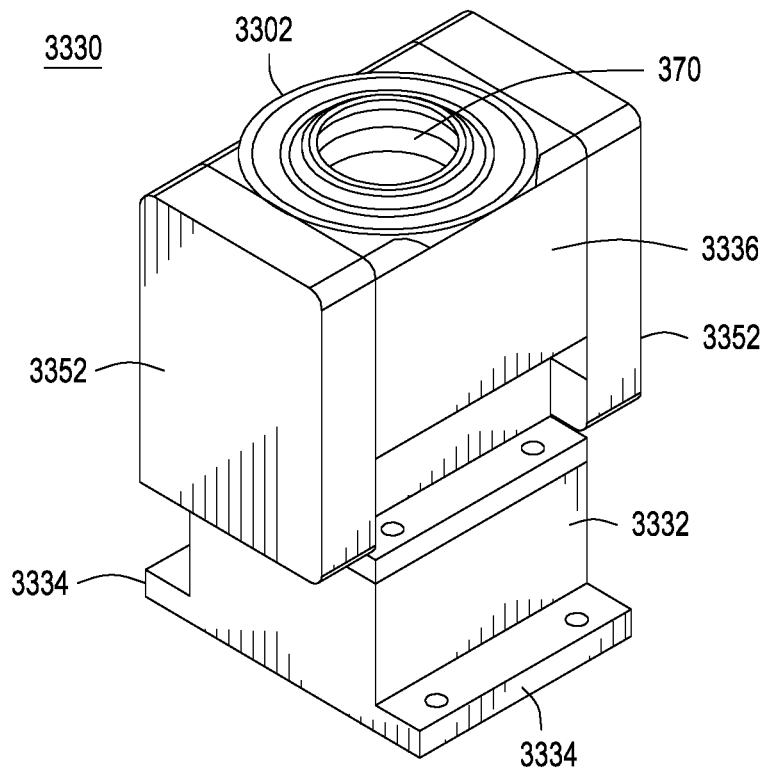
Figure 3G:
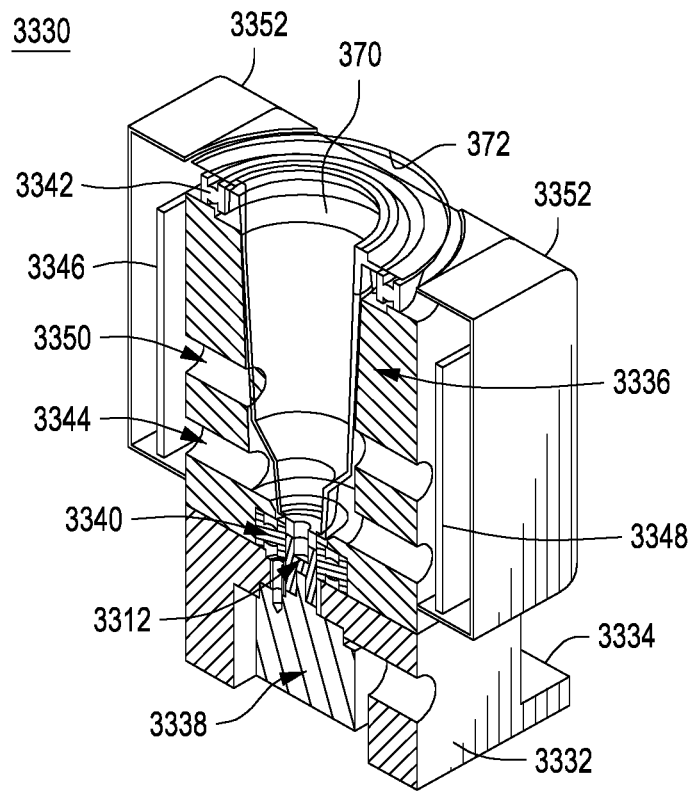

FIG. 3F is a perspective view of one embodiment of a cell growth device 3330. FIG. 3G depicts a cut-away view of the cell growth device 3330 from FIG. 3F. In both figures, the rotating growth vial 370 is seen positioned inside a main housing 3336 with the extended lip 372 of the rotating growth vial 370 extending above the main housing 3336. Additionally, end housings 3352, a lower housing 3332 and flanges 3334 are indicated in both figures. Flanges 3334 are used to attach the cell growth device 3330 to heating/cooling means or other structure (not shown). FIG. 3G depicts additional detail. In FIG. 3G, upper bearing 3342 and lower bearing 3340 are shown positioned within main housing 3336. Upper bearing 3342 and lower bearing 3340 support the vertical load of rotating growth vial 3300. Lower housing 3332 contains the drive motor 3338. The cell growth device 3330 of FIG. 3G comprises two light paths: a primary light path 3344, and a secondary light path 3350. Light path 3344 corresponds to light path 3310 positioned in the constricted portion of the tapered-to-constricted portion of the rotating growth vial 370, and light path 3350 corresponds to light path 3308 in the tapered portion of the tapered-to-constricted portion of the rotating growth. Light paths 3310 and 3308 are not shown in FIG. 3G but may be seen in FIG. 3F. In addition to light paths 3344 and 3350, there is an emission board 3348 to illuminate the light path(s), and detector board 3346 to detect the light after the light travels through the cell culture liquid in the rotating growth vial 370.

The motor 3338 engages with drive mechanism 3312 and is used to rotate the rotating growth vial 3300. In some embodiments, motor 3338 is a brushless DC type drive motor with built-in drive controls that can be set to hold a constant revolution per minute (RPM) between 0 and about 3000 RPM. Alternatively, other motor types such as a stepper, servo, brushed DC, and the like can be used. Optionally, the motor 3338 may also have direction control to allow reversing of the rotational direction, and a tachometer to sense and report actual RPM. The motor is controlled by a processor (not shown) according to, e.g., standard protocols programmed into the processor and/or user input, and the motor may be configured to vary RPM to cause axial precession of the cell culture thereby enhancing mixing, e.g., to prevent cell aggregation, increase aeration, and optimize cellular respiration.

Main housing 3336, end housings 3352 and lower housing 3332 of the cell growth device 3330 may be fabricated from any suitable, robust material including aluminum, stainless steel, and other thermally conductive materials, including plastics. These structures or portions thereof can be created through various techniques, e.g., metal fabrication, injection molding, creation of structural layers that are fused, etc. Whereas the rotating growth vial 370 is envisioned in some embodiments to be reusable, but preferably is consumable, the other components of the cell growth device 3330 are preferably reusable and function as a stand-alone benchtop device or as a module in a multi-module cell processing system.

The processor (not shown) of the cell growth device 3330 may be programmed with information to be used as a "blank" or control for the growing cell culture. A "blank" or control is a vessel containing cell growth medium only, which yields 100% transmittance and 0 OD, while the cell sample will deflect light rays and will have a lower percent transmittance and higher OD. As the cells grow in the media and become denser, transmittance will decrease and OD will increase. The processor (not shown) of the cell growth device 3330—may be programmed to use wavelength values for blanks commensurate with the growth media typically used in cell culture (whether, e.g., mammalian cells, bacterial cells, animal cells, yeast cells, etc.). Alternatively, a second spectrophotometer and vessel may be included in the cell growth device 3330, where the second spectrophotometer is used to read a blank at designated intervals.

Figure 3H:
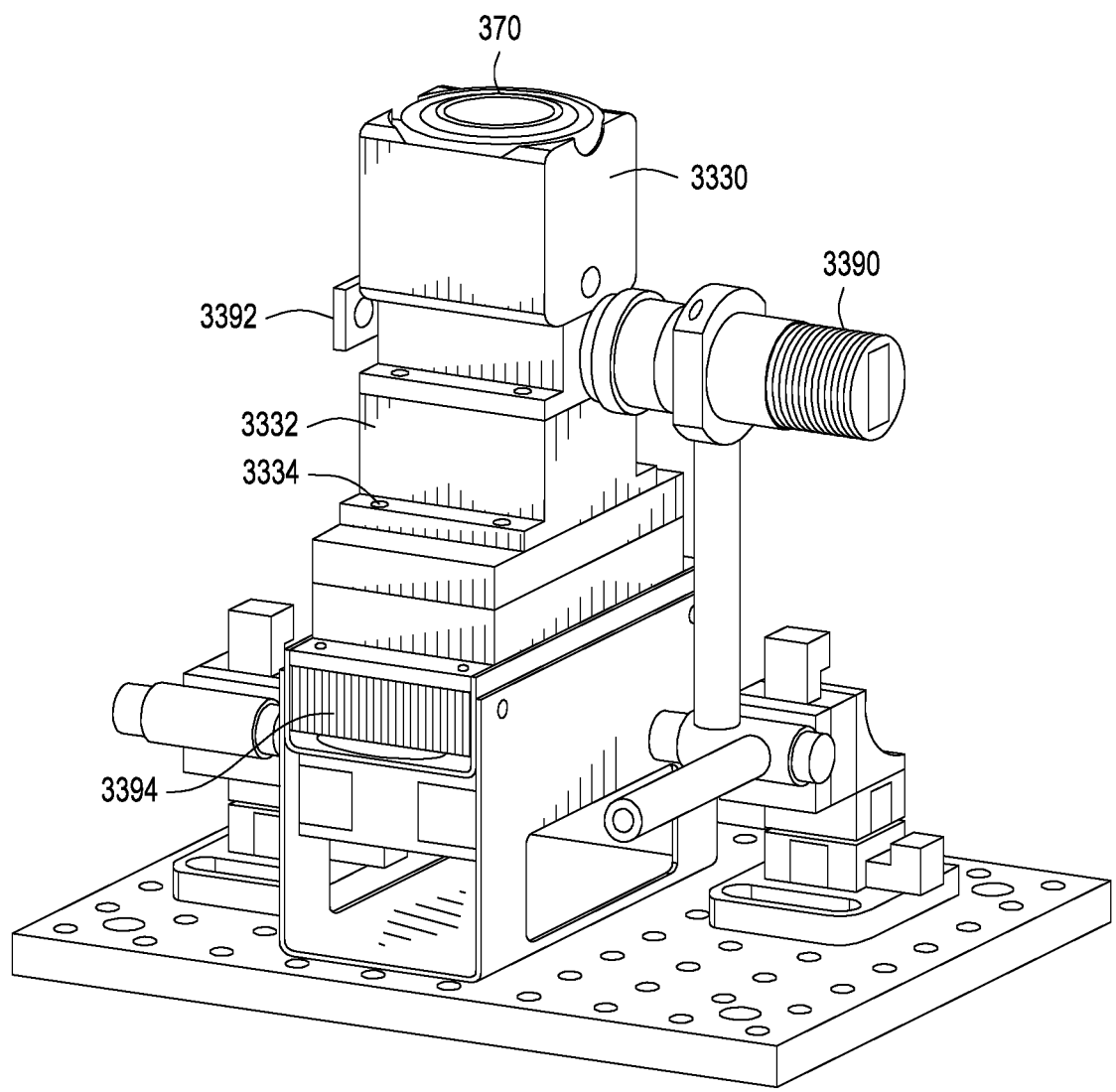

FIG. 3H illustrates a cell growth device 3330 as part of an assembly comprising the cell growth device 3330 of FIG. 3F coupled to light source 3390, detector 3392, and thermal components 3394. The rotating growth vial 370 is inserted into the cell growth device. Components of the light source 3390 and detector 3392 (e.g., such as a photodiode with gain control to cover 5-log) are coupled to the main housing of the cell growth device. The lower housing 3332 that houses the motor that rotates the rotating growth vial 370 is illustrated, as is one of the flanges 3334 that secures the cell growth device 3330 to the assembly. Also, the thermal components 3394 illustrated are a Peltier device or thermoelectric cooler. In this embodiment, thermal control is accomplished by attachment and electrical integration of the cell growth device 3330 to the thermal components 3394 via the flange 3334 on the base of the lower housing 3332.

Thermoelectric coolers are capable of "pumping" heat to either side of a junction, either cooling a surface or heating a surface depending on the direction of current flow. In one embodiment, a thermistor is used to measure the temperature of the main housing and then, through a standard electronic proportional-integral-derivative (PID) controller loop, the rotating growth vial 370 is controlled to approximately +/−0.5° C.

In use, cells are inoculated (cells can be pipetted, e.g., from an automated liquid handling system or by a user) into pre-filled growth media of a rotating growth vial 370 by piercing though the foil seal or film. The programmed software of the cell growth device 3330 sets the control temperature for growth, typically 30° C., then slowly starts the rotation of the rotating growth vial 370. The cell/growth media mixture slowly moves vertically up the wall due to centrifugal force allowing the rotating growth vial 370 to expose a large surface area of the mixture to a normal oxygen environment. The growth monitoring system takes either continuous readings of the OD or OD measurements at pre-set or pre-programmed time intervals. These measurements are stored in internal memory and if requested the software plots the measurements versus time to display a growth curve. If enhanced mixing is required, e.g., to optimize growth conditions, the speed of the vial rotation can be varied to cause an axial precession of the liquid, and/or a complete directional change can be performed at programmed intervals. The growth monitoring can be programmed to automatically terminate the growth stage at a pre-determined OD, and then quickly cool the mixture to a lower temperature to inhibit further growth.

One application for the cell growth device 3330 is to constantly measure the optical density of a growing cell culture. One advantage of the described cell growth device is that optical density can be measured continuously (kinetic monitoring) or at specific time intervals; e.g., every 5, 10, 15, 20, 30 45, or 60 seconds, or every 1, 2, 3, 4, 5, 6, 7, 8, 9, or 10 minutes. While the cell growth device 3330 has been described in the context of measuring the optical density (OD) of a growing cell culture, it should, however, be understood by a skilled artisan given the teachings of the present specification that other cell growth parameters can be measured in addition to or instead of cell culture OD. As with optional measure of cell growth in relation to the solid wall device or module described supra, spectroscopy using visible, UV, or near infrared (NIR) light allows monitoring the concentration of nutrients and/or wastes in the cell culture and other spectroscopic measurements may be made; that is, other spectral properties can be measured via, e.g., dielectric impedance spectroscopy, visible fluorescence, fluorescence polarization, or luminescence. Additionally, the cell growth device 3330 may include additional sensors for measuring, e.g., dissolved oxygen, carbon dioxide, pH, conductivity, and the like. The following US patent documents describe rotating growth vials and cell growth assemblies; Ser. No. 16/360,404, filed 21 Mar. 2019; and Ser. No. 16/360,423, filed 21 Mar. 2019.

Figure 3I:
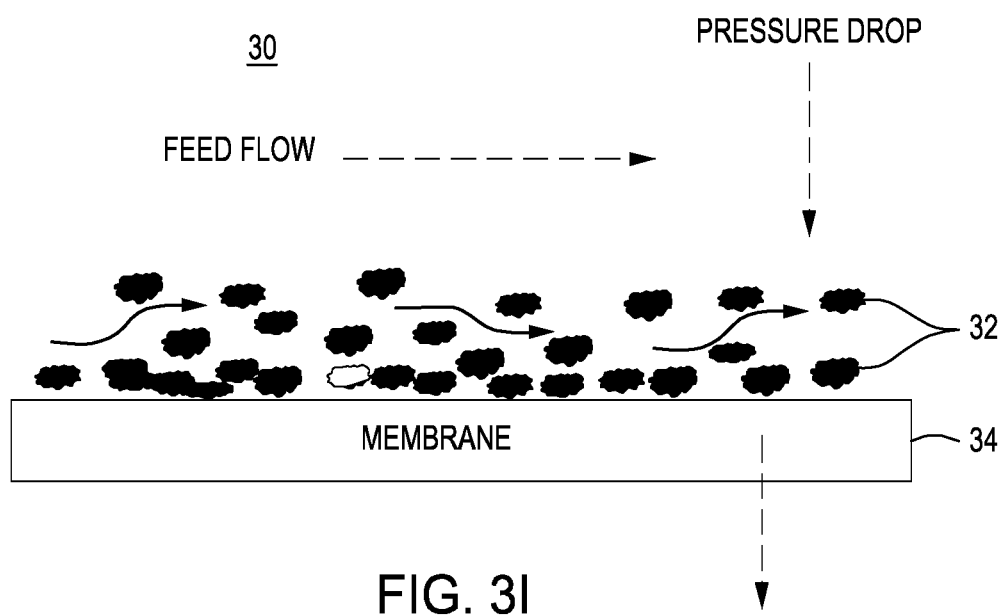

FIG. 3I is a model of tangential flow filtration used in the TFF module described below. The TFF device is an integral module in the automated multi-module cell processing instrument. The TFF is used to concentrate and render electrocompetent cells after growth in the cell growth module. The cells to be concentrated may be cells that were loaded into a rotating growth vial for a first round of editing, or the cells may be cells that have been through one round of editing, recovered from the liquid culture medium, concentrated, and re-grown in a rotating growth vial to be transformed and being prepared for a second round of editing. The TFF device was designed to take into account two primary design considerations. First, the geometry of the TFF device leads to filtering of the cell culture over a large surface area so as to minimize processing time. Second, the design of the TFF device is configured to minimize filter fouling. FIG. 3I is a general model 30 of tangential flow filtration. The TFF device operates using tangential flow filtration, also known as cross-flow filtration. FIG. 3I shows cells flowing over a membrane 34, where the feed flow of the cells 32 in medium or buffer is parallel to the membrane 34. TFF is different from dead-end filtration where both the feed flow and the pressure drop are perpendicular to a membrane or filter.

Figure 3J:
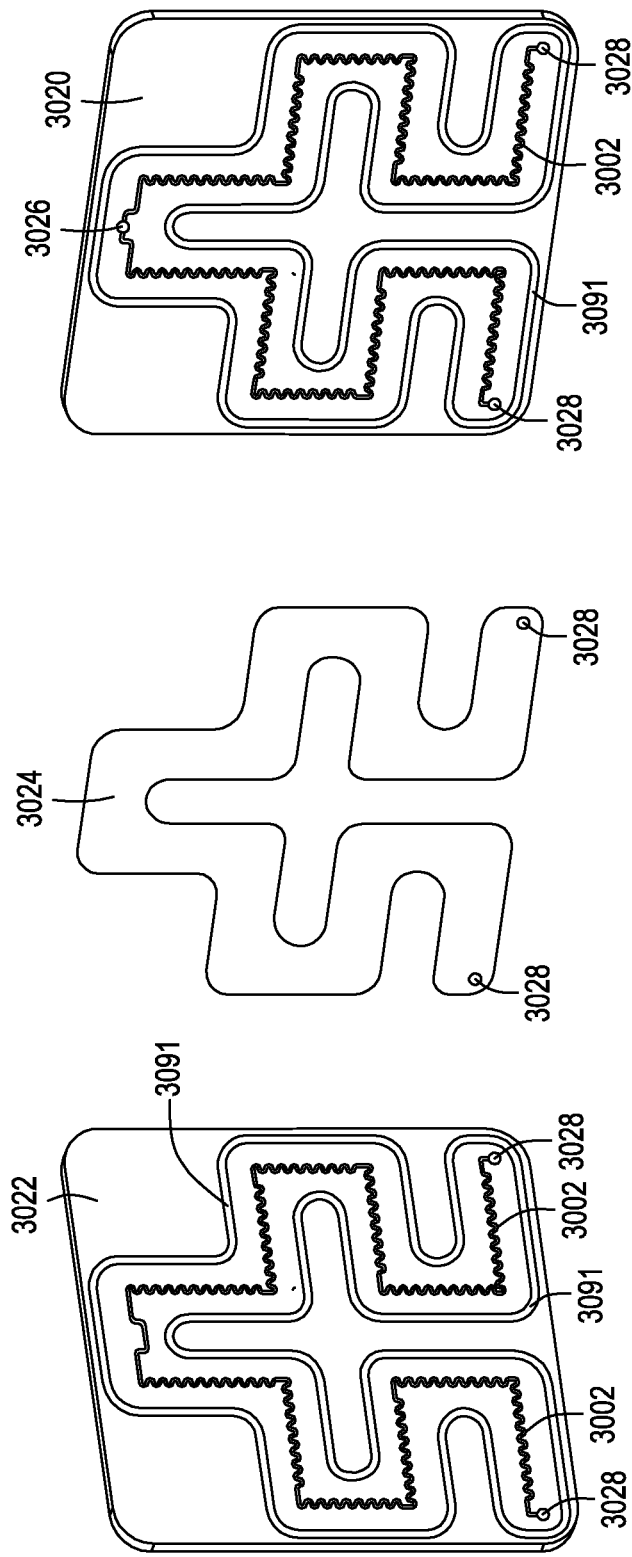

FIGS. 3J-3P depict an embodiment of a tangential flow filtration (TFF) device/module. FIG. 3J depicts a configuration of an retentate member 3022 (on left), a membrane or filter 3024 (middle), and a permeate member 3020 (on the right). In FIG. 3J, retentate member 3022 comprises a tangential flow channel 3002, which has a serpentine configuration that initiates at one lower corner of retentate member 3022—specifically at retentate port 3028—traverses across and up then down and across retentate member 3022, ending in the other lower corner of retentate member 3022 at a second retentate port 3028. Also seen on retentate member 3022 is energy director 3091, which circumscribes the region where membrane or filter 3024 is seated. Energy director 3091 in this embodiment mates with and serves to facilitate ultrasonic wending or bonding of retentate member 3022 with permeate member 3020 via the energy director component on permeate member 3020. Membrane or filter 3024 has through-holes for retentate ports 3028, and is configured to seat within the circumference of energy directors 3091 between the retentate member 3022 and permeate member 3020.

Permeate member 3020 comprises, in addition to energy director 3091, through-holes for retentate port 3028 at each bottom corner (which mate with the through-holes for retentate ports 3028 at the bottom corners of membrane 3024 and retentate ports 3028 in retentate member 3022), as well as a tangential flow channel 3002 and a single permeate port 3026 positioned at the top and center of permeate member 3020. The tangential flow channel 3002 structure in this embodiment has a serpentine configuration and an undulating geometry, although other geometries may be used. In some aspects, the length of the tangential flow channel is from 10 mm to 1000 mm, from 60 mm to 200 mm, or from 80 mm to 100 mm. In some aspects, the width of the channel structure is from 10 mm to 120 mm, from 40 mm to 70 mm, or from 50 mm to 60 mm. In some aspects, the cross section of the tangential flow channel 3002 is rectangular. In some aspects, the cross section of the tangential flow channel 3002 is 5 µm to 1000 µm wide and 5 µm to 1000 µm high, 300 µm to 700 µm wide and 300 µm to 700 µm high, or 400 µm to 600 µm wide and 400 µm to 600 µm high. In other aspects, the cross section of the tangential flow channel 3002 is circular, elliptical, trapezoidal, or oblong, and is 100 µm to 1000 µm in hydraulic radius, 300 µm to 700 µm in hydraulic radius, or 400 µm to 600 µm in hydraulic radius.

Figure 3K:
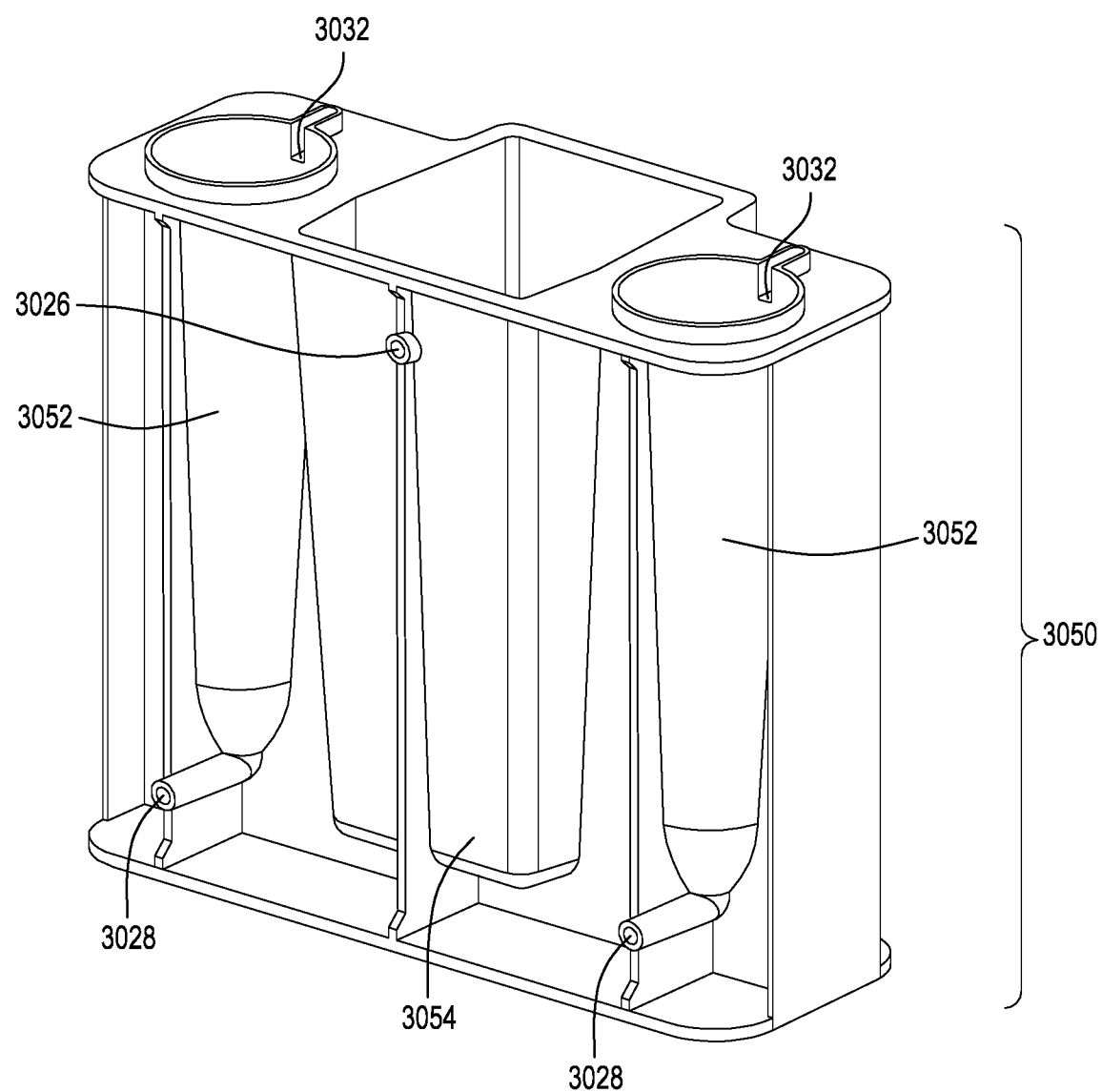

FIG. 3K is a side perspective view of a reservoir assembly 3050. Reservoir assembly 3050 comprises retentate reservoirs 3052 on either side of a single permeate reservoir 3054. Retentate reservoirs 3052 are used to contain the cells and medium as the cells are transferred through the TFF device or module and into the retentate reservoirs during cell concentration. Permeate reservoir 3054 is used to collect the filtrate fluids removed from the cell culture during cell concentration, or old buffer or medium during cell growth. In the embodiment depicted in FIGS. 3J-3P, buffer or medium is supplied to the permeate member from a reagent reservoir separate from the device module. Additionally seen in FIG. 3K are grooves 3032 to accommodate pneumatic ports (not seen), permeate port 3026, and retentate port through-holes 3028. The retentate reservoirs are fluidically coupled to the retentate ports 3028, which in turn are fluidically coupled to the portion of the tangential flow channel disposed in the retentate member (not shown). The permeate reservoir is fluidically coupled to the permeate port 3026 which in turn are fluidically coupled to the portion of the tangential flow channel disposed in permeate member (not shown), where the portions of the tangential flow channels are bifurcated by membrane (not shown). In embodiments including the present embodiment, up to 120 mL of cell culture can be grown and/or filtered, or up to 100 mL, 90 mL, 80 mL, 70 mL, 60 mL, 50 mL, 40 mL, 30 mL or 20 mL of cell culture can be grown and/or concentrated.

Figure 3L:
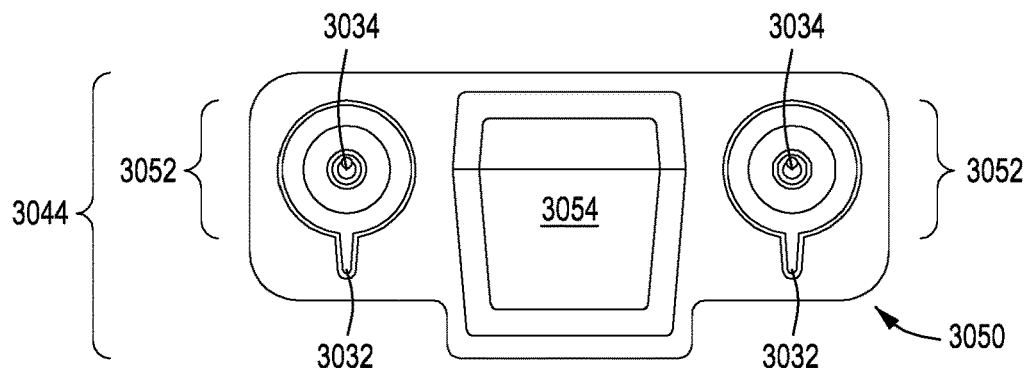
Figure 3M:
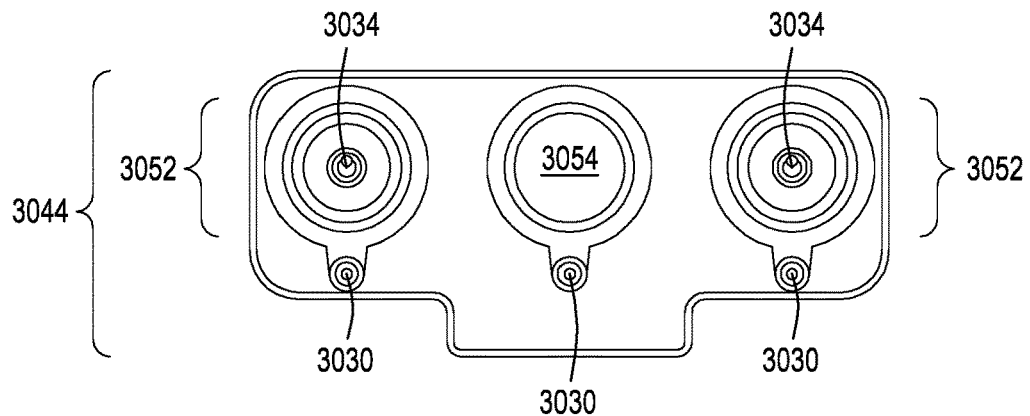
Figure 3N:
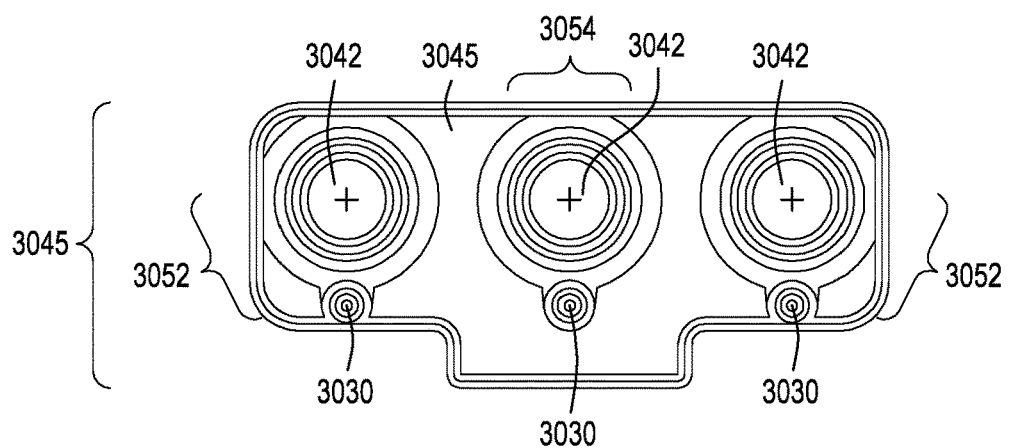

FIG. 3L depicts a top-down view of the reservoir assembly 3050 shown in FIG. 3K, FIG. 3M depicts a cover 3044 for reservoir assembly 3050 shown in FIGS. 3K, and 3N depicts a gasket 3045 that in operation is disposed on cover 3044 of reservoir assembly 3050 shown in FIG. 3K. FIG. 3L is a top-down view of reservoir assembly 3050, showing two retentate reservoirs 3052, one on either side of permeate reservoir 3054. Also seen are grooves 3032 that will mate with a pneumatic port (not shown), and fluid channels 3034 that reside at the bottom of retentate reservoirs 3052, which fluidically couple the retentate reservoirs 3052 with the retentate ports 3028 (not shown), via the through-holes for the retentate ports in permeate member 3220 and membrane 3024 (also not shown). FIG. 3M depicts a cover 3044 that is configured to be disposed upon the top of reservoir assembly 3050. Cover 3044 has round cut-outs at the top of retentate reservoirs 3052 and permeate reservoir 3054. Again, at the bottom of retentate reservoirs 3052 fluid channels 3034 can be seen, where fluid channels 3034 fluidically couple retentate reservoirs 3052 with the retentate ports 3028 (not shown). Also shown are three pneumatic ports 3030 for each retentate reservoir 3052 and permeate reservoir 3054. FIG. 3N depicts a gasket 3045 that is configured to be disposed upon the cover 3044 of reservoir assembly 3050. Seen are three fluid transfer ports 3042 for each retentate reservoir 3052 and for permeate reservoir 3054. Again, three pneumatic ports 3030, for each retentate reservoir 3052 and for permeate reservoir 3054, are shown.

Figure 3O:
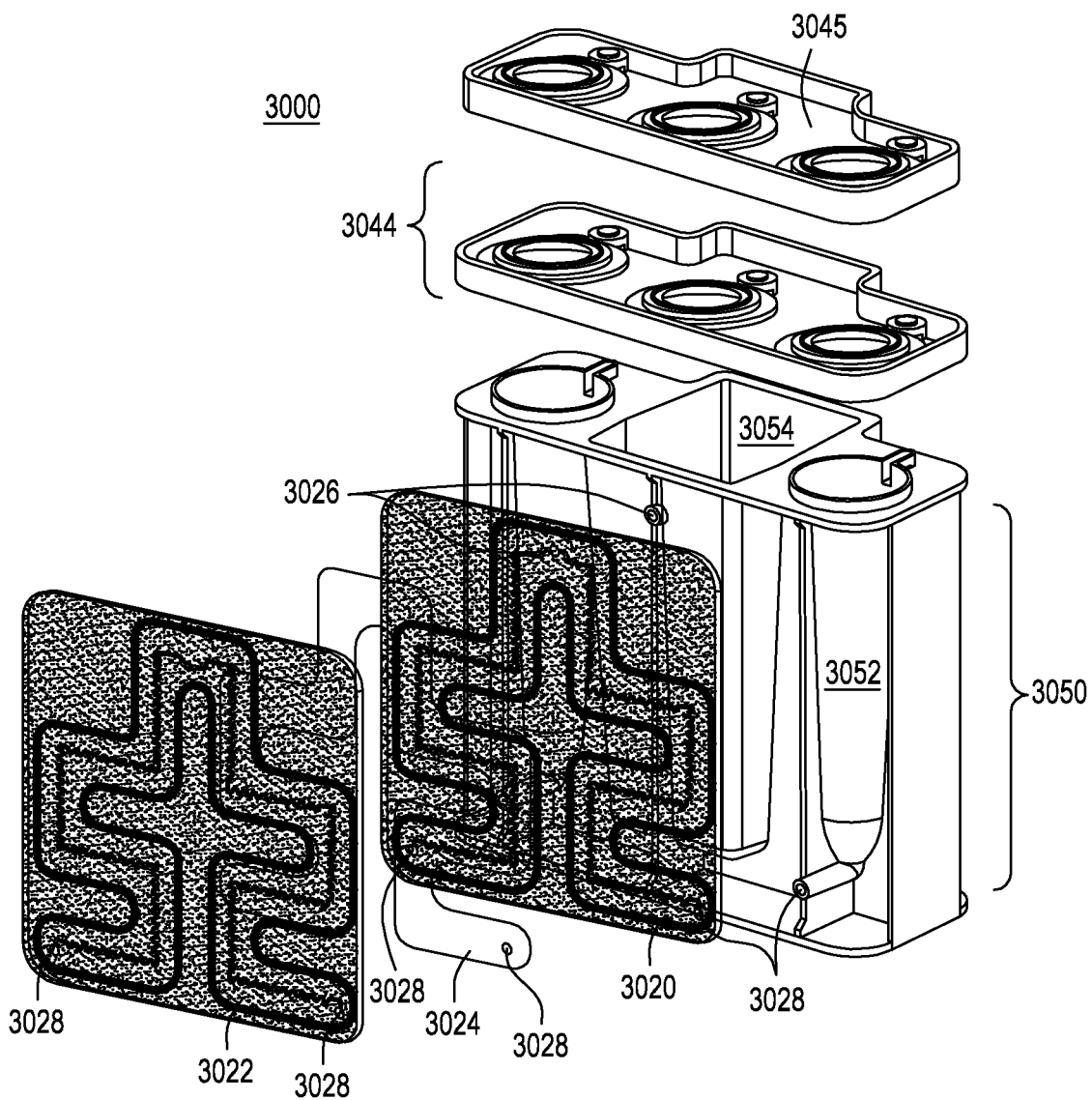

FIG. 3O depicts an exploded view of a TFF module 3000. Seen are components reservoir assembly 3050, a cover 3044 to be disposed on reservoir assembly 3050, a gasket 3045 to be disposed on cover 3044, retentate member 3022, membrane or filter 3024, and permeate member 3020. Also seen is permeate port 3026, which mates with permeate port 3026 on permeate reservoir 3054, as well as two retentate ports 3028, which mate with retentate ports 3028 on retentate reservoirs 3052 (where only one retentate reservoir 3052 can be seen clearly in this FIG. 3O). Also seen are through-holes for retentate ports 3028 in membrane 3024 and permeate member 3020.

Figure 3P:
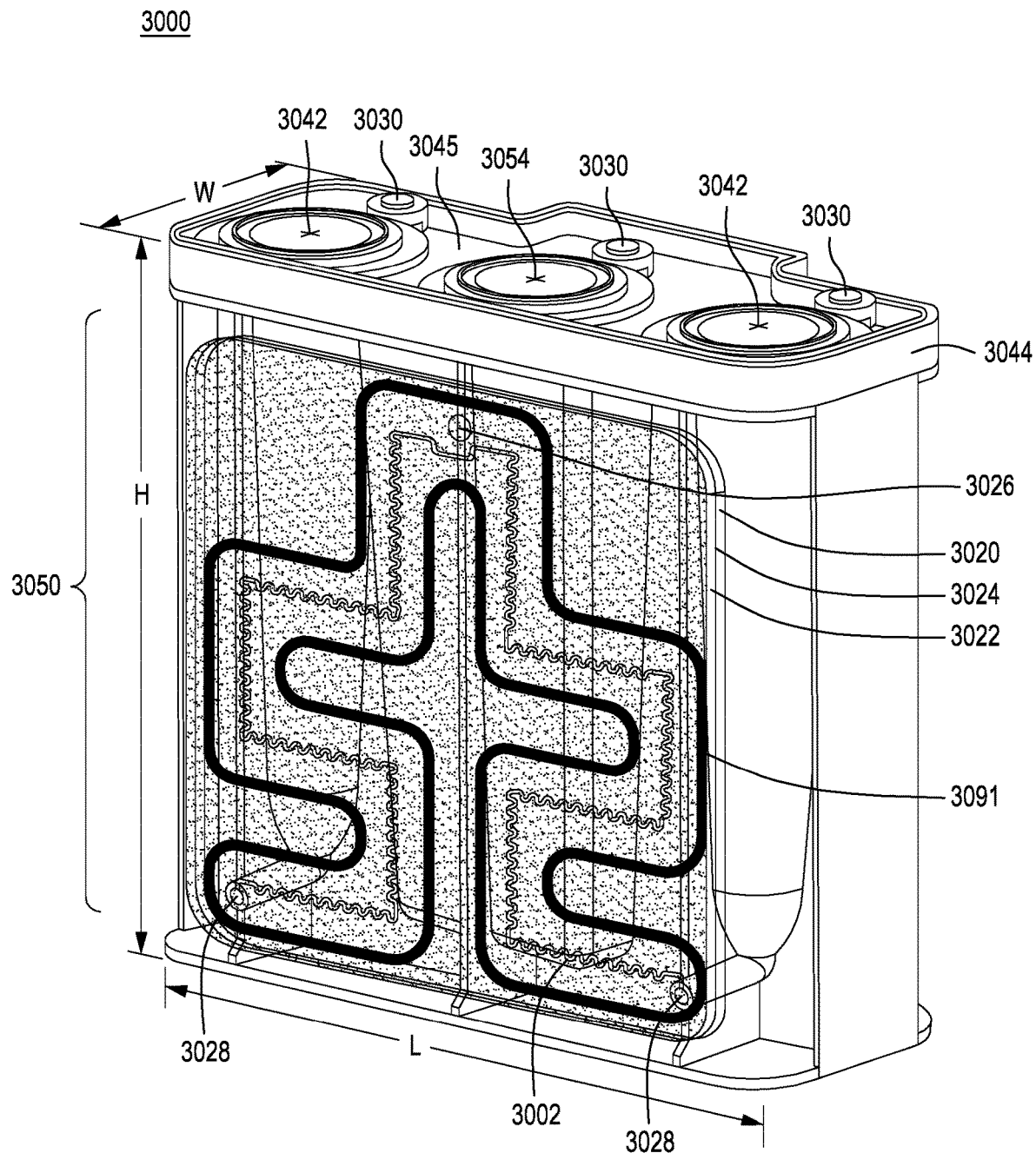

FIG. 3P depicts an embodiment of assembled TFF module 3000. Retentate member 3022, membrane member 3024, and permeate member 3020 are coupled side-to-side with reservoir assembly 3050. Seen are two retentate ports 3028 (which couple the tangential flow channel 3002 in retentate member 3022 to the two retentate reservoirs (not shown), and one permeate port 3026, which couples the tangential flow channel 3002 in permeate/filtrate member 3020 to the permeate reservoir (not shown). Also seen is tangential flow channel 3002, which is formed by the mating of retentate member 3022 and permeate member 3020, with membrane 3024 sandwiched between and bifurcating tangential flow channel 3002. Also seen is energy director 3091, which in this FIG. 3L has been used to ultrasonically weld or couple retentate member 3022 and permeate member 3020, surrounding membrane 3024. Cover 3044 can be seen on top of reservoir assembly 3050, and gasket 3045 is disposed upon cover 3044. Gasket 3045 engages with and provides a fluid-tight seal and pneumatic connections with fluid transfer ports 3042 and pneumatic ports 3030, respectively. FIG. 3P also shows the length, height, and width dimensions of the TFF module 3000. The assembled TFF device 3000 typically is from 50 to 175 mm in height, or from 75 to 150 mm in height, or from 90 to 120 mm in height; from 50 to 175 mm in length, or from 75 to 150 mm in length, or from 90 to 120 mm in length; and is from 30 to 90 mm in depth, or from 40 to 75 mm in depth, or from about 50 to 60 mm in depth. An exemplary TFF device is 110 mm in height, 120 mm in length, and 55 mm in depth. For further information and alternative embodiments on TFFs, see, e.g., U.S. Ser. No. 62/728,365, filed 7 Sep. 2018; 62/857,599, filed 5 Jun. 2019; and 62/867,415, filed 27 Jun. 2019.

Figure 4:
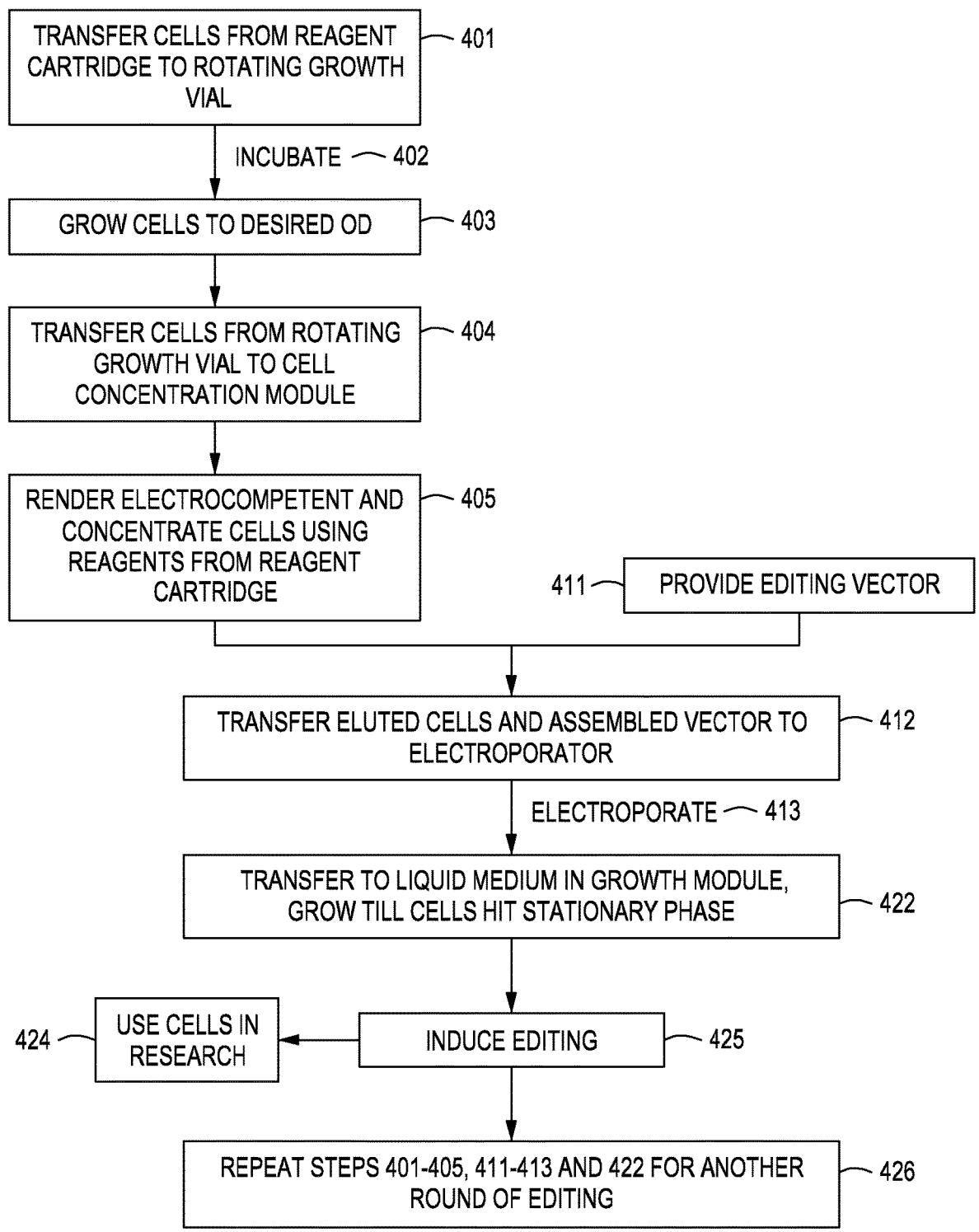
FIG. 4 is a block diagram for a method for creating edits in live cells and screening for edited cells using the automated multi-module system as, e.g., shown in FIG. 3A.

FIG. 4 is a block diagram of one embodiment of a method 400 for using the automated multi-module cell processing instrument of FIG. 3A. In a first step, cells are transferred 401 from reagent cartridge 310 (please refer to FIG. 3A regarding element numbers 300) to growth vial 318. The cells are incubated 402, e.g., until they grow to a desired OD 403. The cells are then transferred 404 to cell concentration module 322 to perform medium or buffer exchange and render the cells competent (e.g., electrocompetent) via medium/buffer exchange while also reducing the volume of the cell sample to a volume appropriate for electroporation, as well as to remove unwanted components, e.g., salts, from the cell sample. Once the cells have been rendered competent and suspended in an appropriate volume for transformation 405, the cell sample is transferred 412 to flow-through electroporation device 330 (transformation module) in reagent cartridge 310.

While cells are being processed for electroporation, one or more editing vectors are provided 411, the assembled editing vectors are transferred 412 to electroporation device 330 in reagent cartridge 310. The assembled vectors (the vector library) and the cells are thus combined in flow-through electroporation device 330 and the flow-through electroporation device is engaged 413.

After electroporation, the transformed cells optionally are transferred to liquid medium to recover from the transformation process and be subjected to selection. The cells are allowed to grow until they reach stationary phase 422—or until the cells nearly reach stationary phase—and at this point editing is induced 425. Once editing has been completed (e.g., ~1-3 hours), the cells can be sequenced, assayed or used in research 424, or steps 401-405, 411-413 and 422 can be repeated for another round of editing 426.

Figure 5:
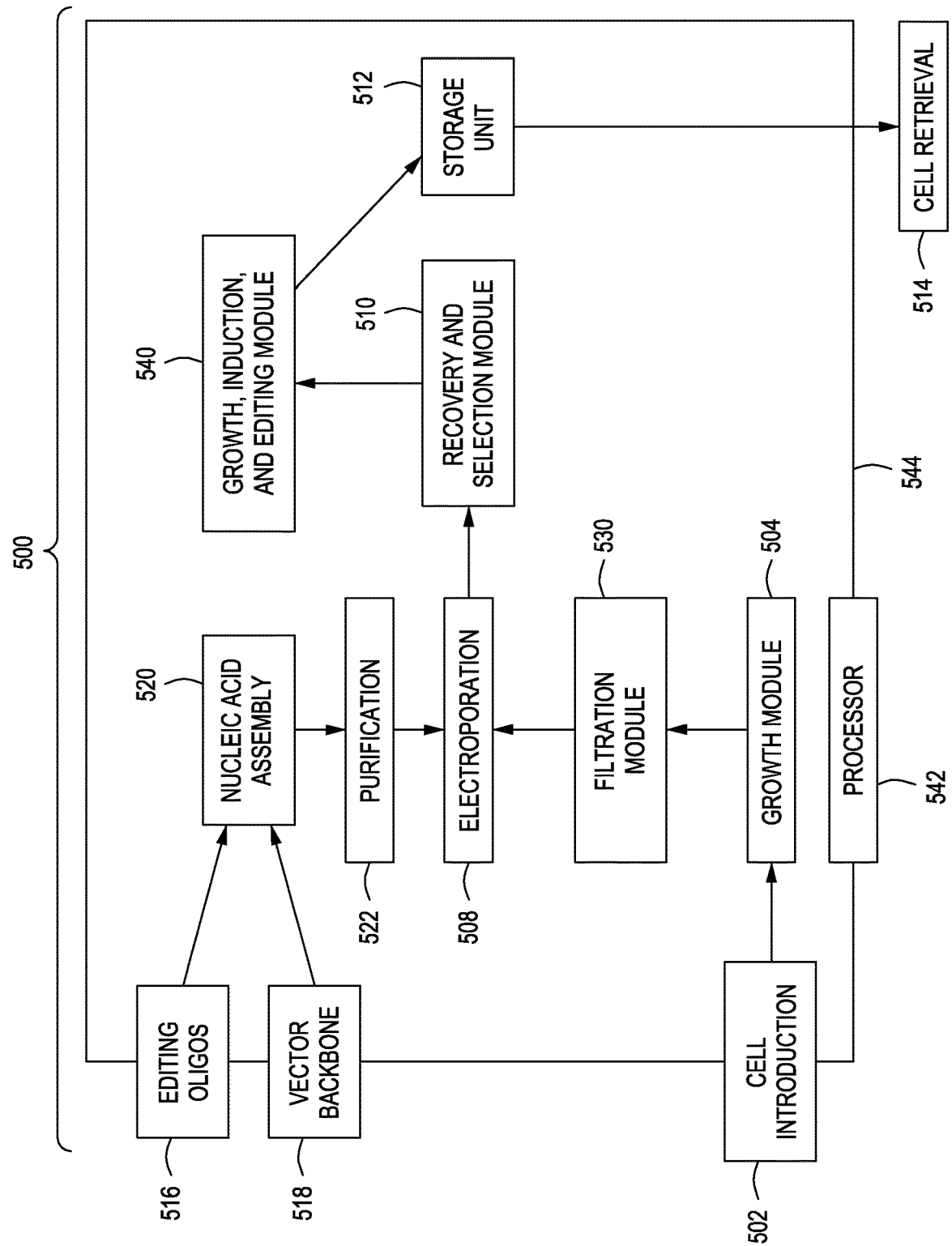
FIG. 5 is a simplified process diagram of an embodiment of an exemplary automated multi-module cell processing instrument.

FIG. 5 is a simplified block diagram of an embodiment of an exemplary automated multi-module cell processing instrument comprising a bulk liquid growth module for induced editing and enrichment for edited cells. The cell processing instrument 500 may include a housing 544, a reservoir of cells to be transformed or transfected 502, and a growth module (a cell growth device) 504. The cells to be transformed are transferred from a reservoir to the growth module to be cultured until the cells hit a target OD. Once the cells hit the target OD, the growth module may cool or freeze the cells for later processing, or the cells may be transferred to a filtration or concentration module 530 where the cells are rendered electrocompetent and concentrated to a volume optimal for cell transformation. Once concentrated, the cells are then transferred to an electroporation device 508 (e.g., transformation/transfection module).

In addition to the reservoir for storing the cells, the system 500 may include a reservoir for storing editing cassettes 516 and a reservoir for storing an expression vector backbone 518. Both the editing oligonucleotide cassettes and the expression vector backbone are transferred from the reagent cartridge to a nucleic acid assembly module 520, where the editing oligonucleotide cassettes are inserted into the expression vector backbone. The assembled nucleic acids may be transferred into an optional purification module 522 for desalting and/or other purification and/or concentration procedures needed to prepare the assembled nucleic acids for transformation. Alternatively, pre-assembled nucleic acids, e.g., an editing vector, may be stored within reservoir 516 or 518. Once the processes carried out by the purification module 522 are complete, the assembled nucleic acids are transferred to, e.g., an electroporation device 508, which already contains the cell culture grown to a target OD and rendered electrocompetent via filtration module 530. In electroporation device 508, the assembled nucleic acids are introduced into the cells. Following electroporation, the cells are transferred into a combined recovery/selection module 510.

Following recovery, and, optionally, selection, the cells are transferred to a growth, induction, and editing module (bulk liquid culture) 540. The cells are allowed to grow until the cells reach the stationary growth phase (or nearly so), then editing is induced by induction of transcription of one or both of the nuclease and gRNA. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, induction, editing and storage modules may all be separate, may be arranged and combined as shown in FIG. 5, or may be arranged or combined in other configurations. In certain embodiments, recovery and selection are performed in one module, and growth, editing, and re-growth are performed in a separate module. Alternatively, recovery, selection, growth, editing, and re-growth are performed in a single module.

Once the cells are edited and re-grown (e.g., recovered from editing), the cells may be stored, e.g., in a storage module 512, where the cells can be kept at, e.g., 4° C. until the cells are retrieved for further study. Alternatively, the cells may be used in another round of editing. The multi-module cell processing instrument is controlled by a processor 542 configured to operate the instrument based on user input, as directed by one or more scripts, or as a combination of user input or a script. The processor 542 may control the timing, duration, temperature, and operations of the various modules of the system 500 and the dispensing of reagents. For example, the processor 542 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

The automated multi-module cell processing instrument 500 is a nuclease-directed genome editing system and can be used in single editing systems where, e.g., two or more edits to a cellular genome are introduced using a single editing process via multiplex editing cassettes. The system may be configured to perform sequential editing, e.g., using different nuclease-directed systems sequentially to provide two or more genome edits in a cell in each of two or more rounds of editing; and/or recursive editing, e.g. utilizing a single nuclease-directed system to introduce sequentially two or more genome edits in a cell in each of two or more round of editing.

It should be apparent to one of ordinary skill in the art given the present disclosure that the process described may be recursive and multiplexed; that is, cells may go through the workflow described in relation to FIG. 5, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries.

In any recursive process, it is advantageous to "cure" the previous engine and editing vectors (or single engine+editing vector in a single vector system). "Curing" is a process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine plasmid. For curing methods appropriate for use in the methods described herein see, e.g., U.S. Ser. No. 62/857,967, filed 6 Jun. 2018.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Other equivalent methods, steps and compositions are intended to be included in the scope of the invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1: Editing Cassette and Backbone Amplification and Assembly

Editing Cassette Preparation:

5 nM of oligonucleotides synthesized on a chip were amplified using Q5 polymerase in 50 μL volumes. The PCR conditions were 95° C. for 1 minute; 8 rounds of 95° C. for 30 seconds/60° C. for 30 seconds/72° C. for 2.5 minutes; with a final hold at 72° C. for 5 minutes. Following amplification, the PCR products were subjected to SPRI cleanup, where 30 μL SPRI mix was added to the 50 μL PCR reactions and incubated for 2 minutes. The tubes were subjected to a magnetic field for 2 minutes, the liquid was removed, and the beads were washed 2× with 80% ethanol, allowing 1 minute between washes. After the final wash, the beads were allowed to dry for 2 minutes, 50 μL 0.5× TE pH 8.0 was added to the tubes, and the beads were vortexed to mix. The slurry was incubated at room temperature for 2 minutes, then subjected to the magnetic field for 2 minutes. The eluate was removed and the DNA quantified.

Following quantification, a second amplification procedure was carried out using a dilution of the eluate from the SPRI cleanup. PCR was performed under the following conditions: 95° C. for 1 minute; 18 rounds of 95° C. for 30 seconds/72° C. for 2.5 minutes; with a final hold at 72° C. for 5 minutes. Amplicons were checked on a 2% agarose gel and pools with the cleanest output(s) were identified. Amplification products appearing to have heterodimers or chimeras were not used.

Backbone Preparation:

A 10-fold serial dilution series of purified backbone was performed, and each of the diluted backbone series was amplified under the following conditions: 95° C. for 1 minute; then 30 rounds of 95° C. for 30 seconds/60° C. for 1.5 minutes/72° C. for 2.5 minutes; with a final hold at 72° C. for 5 minutes. After amplification, the amplified backbone was subjected to SPRI cleanup as described above in relation to the cassettes. The backbone was eluted into 100 μL ddH$_2$O and quantified before isothermal nucleic acid assembly.

Isothermal Assembly:

150 ng backbone DNA was combined with 100 ng cassette DNA. An equal volume of 2× isothermal nucleic acid assembly master Mmix was added, and the reaction was incubated for 45 minutes at 50° C. After assembly, the assembled backbone and cassettes were subjected to SPRI cleanup, as described above.

Example 2: Transformation of Editing Vector Library into E Cloni®

Transformation:

20 μL of the prepared editing vector Gibson Assembly reaction was added to 30 μL chilled water along with 10 μL E Cloni® (Lucigen, Middleton, WI) supreme competent cells. An aliquot of the transformed cells was spot plated to check the transformation efficiency, where >100× coverage was required to continue. The transformed E Cloni® cells were outgrown in 25 mL SOB+100 μg/mL carbenicillin (carb). Glycerol stocks were generated from the saturated culture by adding 500 μL 50% glycerol to 1000 μL saturated overnight culture. The stocks were frozen at −80° C. This step is optional, providing a ready stock of the cloned editing library. Alternatively, isothermal or another assembly of the editing cassettes and the vector backbone can be performed before each editing experiment.

Example 3: Creation of New Cell Line Transformed with Engine Vector

Transformation:

1 µL of the engine vector DNA (comprising a coding sequence for MAD7 nuclease under the control of the pL inducible promoter, a chloramphenicol resistance gene, and the λ Red recombineering system) was added to 50 µL EC1 strain E. coli cells. The transformed cells were plated on LB plates with 25 µg/mL chloramphenicol (chlor) and incubated overnight to accumulate clonal isolates. The next day, a colony was picked, grown overnight in LB+25 µg/mL chlor, and glycerol stocks were prepared from the saturated overnight culture by adding 500 µL 50% glycerol to 1000 µL culture. The stocks of EC1 comprising the engine vector were frozen at −80° C.

Example 4: Preparation of Competent Cells

A 1 mL aliquot of a freshly-grown overnight culture of EC1 cells transformed with the engine vector was added to a 250 mL flask containing 100 mL LB/SOB+25 µg/mL chlor medium. The cells were grown to 0.4-0.7 OD, and cell growth was halted by transferring the culture to ice for 10 minutes. The cells were pelleted at 8000× g in a JA-18 rotor for 5 minutes, washed 3× with 50 mL ice cold ddH$_2$O or 10% glycerol, and pelleted at 8000× g in JA-18 rotor for 5 minutes. The washed cells were resuspended in 5 mL ice cold 10% glycerol and aliquoted into 200 µL portions. Optionally at this point the glycerol stocks could be stored at −80° C. for later use.

Example 5: Bulk Liquid Protocol: Induction and Outgrowth 250 mL baffled shake flasks were prepared with 50 mL of SOB+100 µg/mL carbenicillin and 25 µg/mL chloramphenicol. For a full, deconvolution experiment, 3 shake flasks were prepared per transformation. 500 µL of undiluted culture from each transformation reaction was transferred into the prepared 250 mL shake flasks. The following temperature settings were set up on an incubator: 30° C. for 9 hours→42° C. for 2 hours→30° C. for 9 hours. This temperature regime was used to allow for additional recovery of the cells from transformation during the first eight hours. The lambda red system was induced one hour prior to induction of the nuclease, where lambda induction was triggered by the addition of arabinose (2.5 mL of 20% arabinose) to the culture, and the nuclease induction was triggered by increasing the temperature of the cultures to 42° C. For full deconvolution experiments, arabinose was not added to the UPTAKE and CUT flasks as those should not express lambda red; further, the UPTAKE flasks were not shifted to 42° C.

After the temperature cycling is complete (~21 hours), the shake flasks were removed. For NGS-SinglePlex: serial dilutions of $10^{-5}$ to $10^{-7}$ of each culture were prepared with 0.8% NaCl (50 µL of culture into 450 µL of sterile, 0.8% NaCl). Following dilution, 300 µL of each dilution was plated onto 150 mm LB agar plates with standard concentrations of chloramphenicol and carbenicillin. The plates were then placed in a 30° C. incubator for overnight growth and were picked for singleplex NGS the following day. For NGS-Amplicon: 250 µL of culture from each shake flask was removed and used as the input for a plasmid extraction protocol. The OD of this culture was measured to select a volume based on the desired number of cells to go into the plasmid purification. Optionally, an undiluted volume from each shake flask may be plated to see enrichment/depletion of cassettes and the plates were scraped the following day and processed.

Figure 6A:
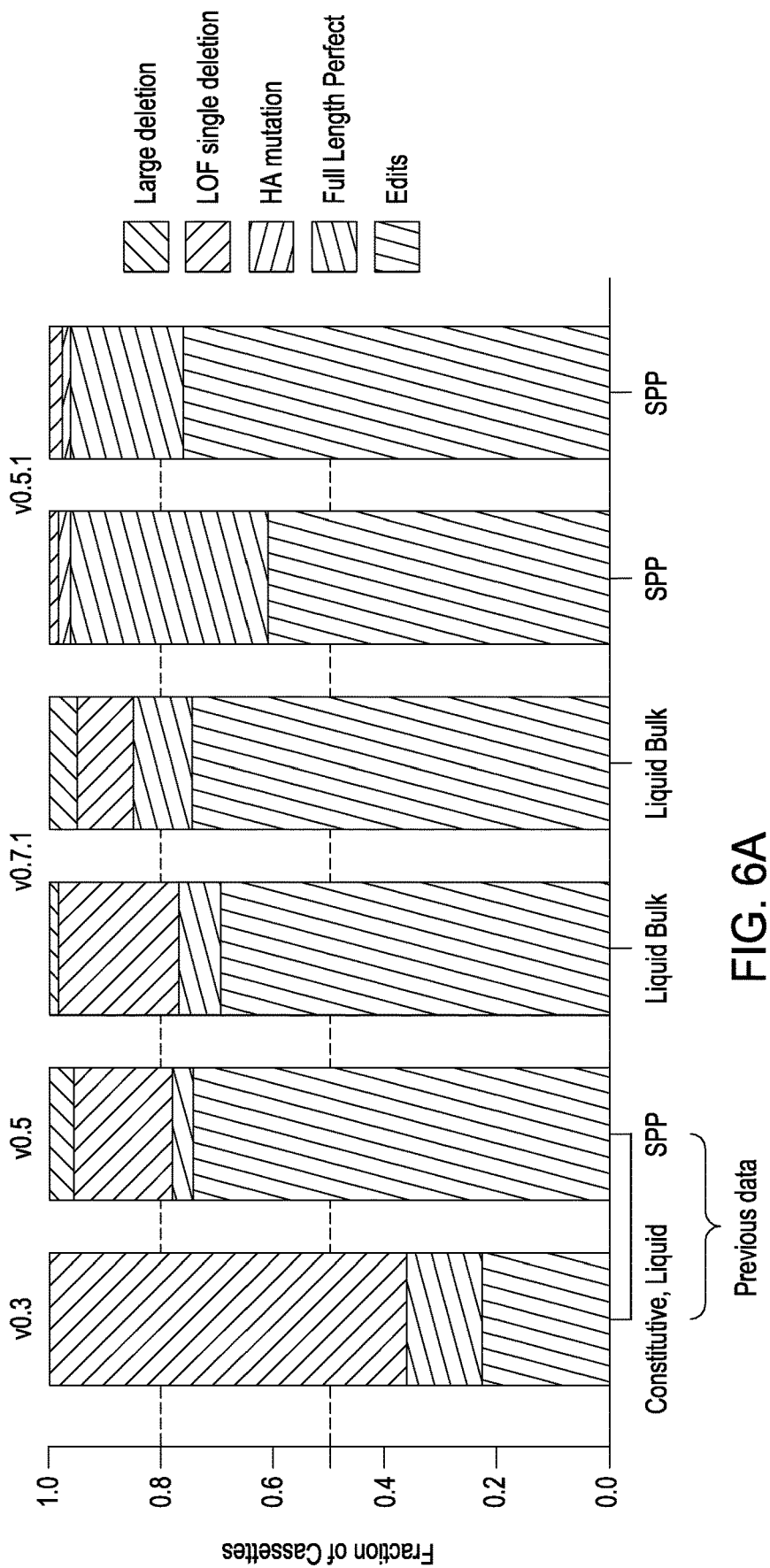
FIGS. 6A and 6B are graphs showing the editing results obtained via the liquid bulk method for increasing observed editing in live cells.
Figure 6B:
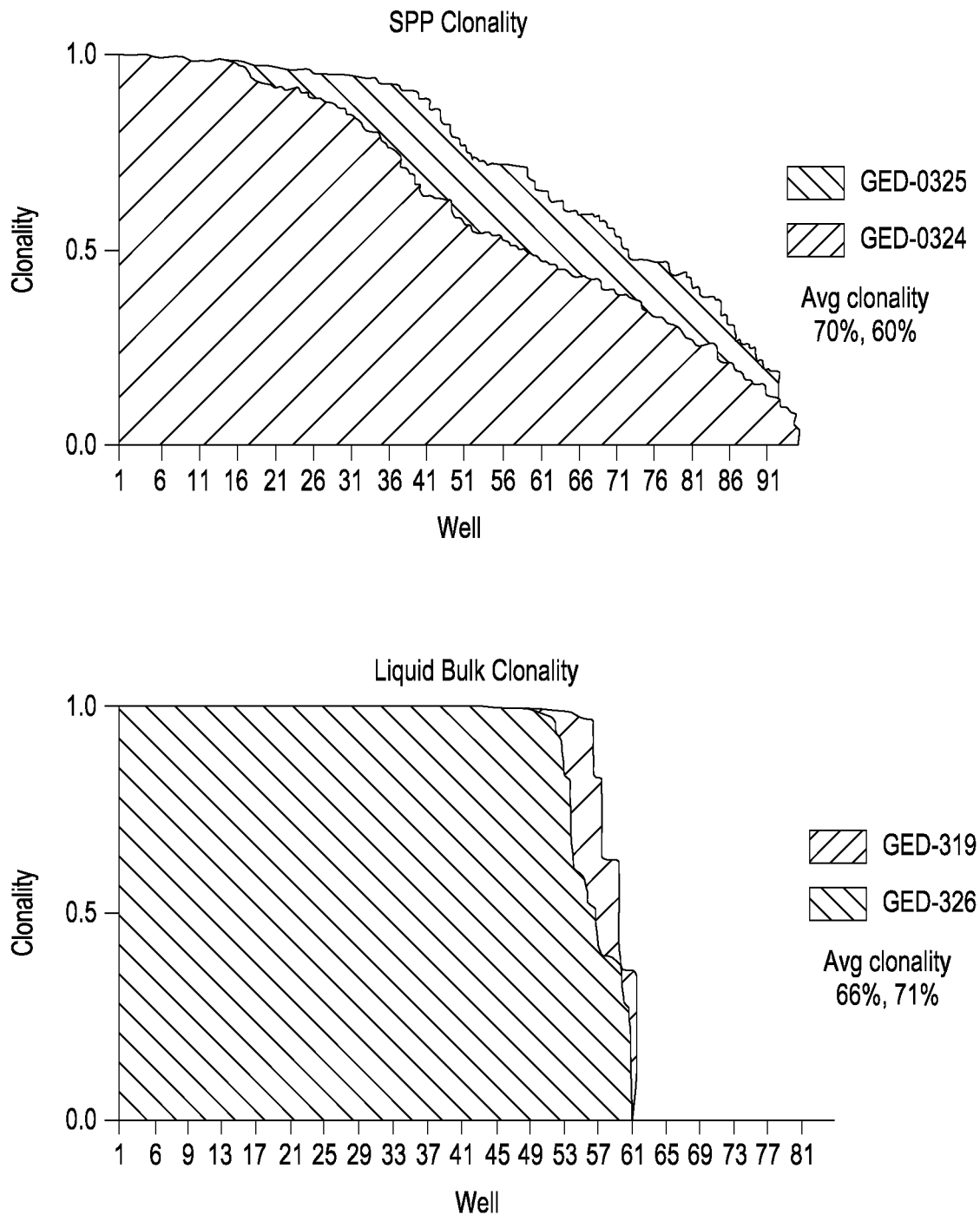

FIG. 6A is a bar graph showing the various types of edits observed using constitutive editing in a liquid culture (approximately 20% editing observed), standard plating procedure (approximately 76% editing observed), two replica experiments of induced editing in liquid bulk (approximately 70% and 76% editing observed), and two replica experiments of induced editing using the standard plating procedure (approximately 60% and 76% editing observed). FIG. 6B shows two graphs of editing clonality. The editing clonality of the standard plating procedure (top) shows mixed clonality for the 96 wells, with some colonies achieving 100% clonality (wells 1-21), most colonies achieving greater than 50% clonality (wells 1-56), and an average clonality of 70% and 60% for the two replicates. The editing clonality of the liquid bulk procotol shows that the majority of the cells were either 100% edited, or 0% edited (e.g., wildtype), with a small number (approximately 8%) between 100% or 0%. Note that the average editing efficiency was similar for these protocols.

Example 6: Fully-Automated Singleplex RGN-Directed Editing Run

Singleplex automated genomic editing using MAD7 nuclease was successfully performed with an automated multi-module instrument of the disclosure. See U.S. Pat. No. 9,982,279.

An ampR plasmid backbone and a lacZ_F172* editing cassette were assembled via Gibson Assembly® into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent E. Coli cells were transferred into a transformation module for electroporation. The transformation module comprised an ADP-EPC cuvette. See, e.g., U.S. Pat No. 62/551,069. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-0.3}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example 7: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent E. Coli cells were transferred into a transformation module for electroporation. The transformation module comprised an ADP-EPC cuvette. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent E. Coli cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method for performing enrichment of cells edited by a nucleic acid-guided nuclease comprising:
    (a) providing transformed cells in growth medium, wherein the cells comprise a coding sequence for a nucleic acid-guided nuclease, a sequence for a donor DNA, and a coding sequence for a gRNA, wherein at least the coding sequence for the gRNA is under the control of an inducible promoter;
    (b) allowing the transformed cells to grow until the cells are in stationary phase;
    (c) inducing transcription of the coding sequence for the gRNA; and
    (d) allowing the cells to edit, wherein an editing efficiency is improved compared to inducing transcription of the coding sequence for the gRNA when the transformed cells are in log phase.

2. The method of claim 1, wherein the coding sequence for a nucleic acid-guided nuclease, the sequence for a donor DNA, and the coding sequence for the gRNA are provided to the cells on a single vector.

3. The method of claim 1, wherein the cells are bacterial cells, yeast cells, or mammalian cells.

4. The method of claim 1, wherein the inducible promoter comprises a first inducible promoter, and wherein the method further comprises rendering the transformed cells electrocompetent and transforming the cells with one or more nucleic acid-guided editing components under the control of a second inducible promoter after step (b).

5. The method of claim 1, wherein the inducible promoter is a promoter that is activated upon an increase in temperature.

6. The method of claim 1, wherein the inducible promoter is a pL promoter.

7. The method of claim 5, wherein transcription is induced by raising the temperature of the cells to 42° C.

8. The method of claim 1, wherein the inducible promoter is a promoter that is activated upon adding an inducing moiety.

9. A method for performing enrichment of cells edited by a nucleic acid-guided nuclease comprising:
  (a) providing transformed cells in growth medium, wherein the cells comprise a first round of nucleic acid-guided editing components, wherein the first round of nucleic acid-guided editing components comprises a first gRNA under the control of a first inducible promoter;
  (b) allowing the transformed cells to grow until the cells are in stationary phase;
  (c) inducing transcription of the first gRNA;
  (d) allowing the cells to edit, wherein an editing efficiency is improved compared to inducing transcription of the first gRNA when the transformed cells are in log phase; and
  (e) transforming the cells with a second round of nucleic acid-guided editing components, wherein the second round of nucleic acid-guided editing components comprises a second gRNA under the control of a second inducible promoter.

10. The method of claim 9, wherein the cells are bacterial cells, yeast cells, or mammalian cells.

11. The method of claim 9, wherein the first round of nucleic acid-guided editing components are encoded on a single vector.

12. The method of claim 9, wherein the second round of nucleic acid-guided editing components are encoded on a single vector.

13. The method of claim 9, wherein the first round of nucleic acid-guided editing components and the second round of nucleic acid-guided editing components are encoded on separate vectors.

14. The method of claim 9, wherein the first inducible promoter, the second inducible promoter, or both, are promoters activated upon an increase in temperature.

15. The method of claim 9, wherein the first inducible promoter, the second inducible promoter, or both, are pL promoters.

16. The method of claim 14, wherein transcription is induced by raising the temperature of the cells to 42° C.

17. The method of claim 9, wherein the first inducible promoter, the second inducible promoter, or both, are promoters activated upon adding an inducing moiety.

* * * * *